(12) United States Patent
Burshteyn et al.

(10) Patent No.: US 6,692,968 B2
(45) Date of Patent: Feb. 17, 2004

(54) APPARATUS AND METHOD FOR SAMPLE PURIFICATION AND ANALYSIS

(75) Inventors: Alexander Burshteyn, Hialeah, FL (US); John W. Joubran, Escondido, CA (US); Nazle Kuylen, Miami, FL (US); Frank J. Lucas, Boca Raton, FL (US); Carlos L. Aparicio, Miami, FL (US); Michael L. Bell, Fullerton, CA (US); Ravinder Gupta, Pembroke Pines, FL (US); Maria Elena Insausti, Miami, FL (US); Jack D. McNeal, Long Beach, CA (US); Paul W. Price, Miami, FL (US); Sandra Socarras, Miami, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/957,234

(22) Filed: Sep. 20, 2001

(65) Prior Publication Data

US 2002/0123154 A1 Sep. 5, 2002

Related U.S. Application Data

(63) Continuation-in-part of application No. 09/611,847, filed on Jul. 7, 2000.

(51) Int. Cl.[7] ................................................. G01N 1/34
(52) U.S. Cl. ......................... 436/63; 210/767; 422/101; 435/308.1; 436/178
(58) Field of Search .................. 436/178, 63, 524–534; 422/101; 435/308.1; 210/767

(56) References Cited

U.S. PATENT DOCUMENTS 4,680,025 A  7/1987  Kruger et al.

(List continued on next page.)

FOREIGN PATENT DOCUMENTS

GB  2210805 A  *  6/1989

OTHER PUBLICATIONS

Fisher 88 Scientific Catalog (1988), pp. 424–425.*
A/G Technology Corporation "(UF/MF) Operating Guide", (OG1/99R2), Jan. 1999.
"Flow Cytometry and Sorting", Melamed, et al., New York-:Wiley–Liss, Inc. (2nd ed., 1990).
Shapiro, H.M., "Practical Flow Cytometry", New York:Wiley–Liss, Inc. (3rd ed., 1995).
Legallais, et al., "Strategies for the depyrogenation of contaminated immunoglobulin G solutions by histidine–immobilized hollow fiber membrane", *Journal of Chromatography B*, Elsevier Science B.V., 691 (1997), pp. 33–41.

*Primary Examiner*—Jan Ludlow
(74) *Attorney, Agent, or Firm*—Howson and Howson; Mitchell E. Alter

(57) ABSTRACT

A method for utilizing a filtration device for removing interferants from a test sample containing a mixture of a composition of interest and interferants in an automated apparatus is disclosed. The filtration device includes a microporous hollow fiber membrane having a plurality of pores sized to retain the composition of interest while allowing smaller diameter interferants to pass through the membrane.

10 Claims, 24 Drawing Sheets

U.S. PATENT DOCUMENTS

| | | | |
|---|---|---|---|
| 4,755,300 A | 7/1988 | Fischel et al. | |
| 4,776,964 A | 10/1988 | Schoendorfer et al. | |
| 4,808,307 A | 2/1989 | Fischel et al. | |
| 4,846,786 A | 7/1989 | Freed et al. | |
| 4,851,126 A | 7/1989 | Schoendorfer | |
| 4,871,462 A | 10/1989 | Fischel et al. | |
| 4,944,883 A | 7/1990 | Schoendorfer et al. | |
| 5,034,135 A | 7/1991 | Fischel | |
| 5,149,661 A | * 9/1992 | Gjerde et al. | |
| 5,190,657 A | 3/1993 | Heagle et al. | |
| 5,192,439 A | 3/1993 | Roth et al. | |
| 5,240,856 A | 8/1993 | Goffe et al. | |
| 5,258,127 A | 11/1993 | Gsell et al. | |
| 5,288,403 A | 2/1994 | Ohno | |
| 5,290,449 A | 3/1994 | Heagle et al. | |
| 5,362,406 A | 11/1994 | Gsell et al. | |
| 5,454,946 A | 10/1995 | Heagle et al. | |
| 5,601,727 A | * 2/1997 | Bormann et al. | |
| 5,674,173 A | 10/1997 | Hlavinka et al. | |
| 5,686,238 A | 11/1997 | Martinson et al. | |
| 5,695,989 A | 12/1997 | Kalamasz | |
| 5,744,047 A | 4/1998 | Gsell et al. | |
| 5,747,349 A | 5/1998 | van den Engh et al. | |
| 5,753,014 A | 5/1998 | Van Rijn | |
| 5,785,869 A | 7/1998 | Martinson et al. | |
| 5,811,061 A | 9/1998 | Martinson et al. | |
| 6,068,775 A | 5/2000 | Custer et al. | |
| 6,153,442 A | * 11/2000 | Pirio et al. | |
| 6,165,796 A | 12/2000 | Bell | |

\* cited by examiner

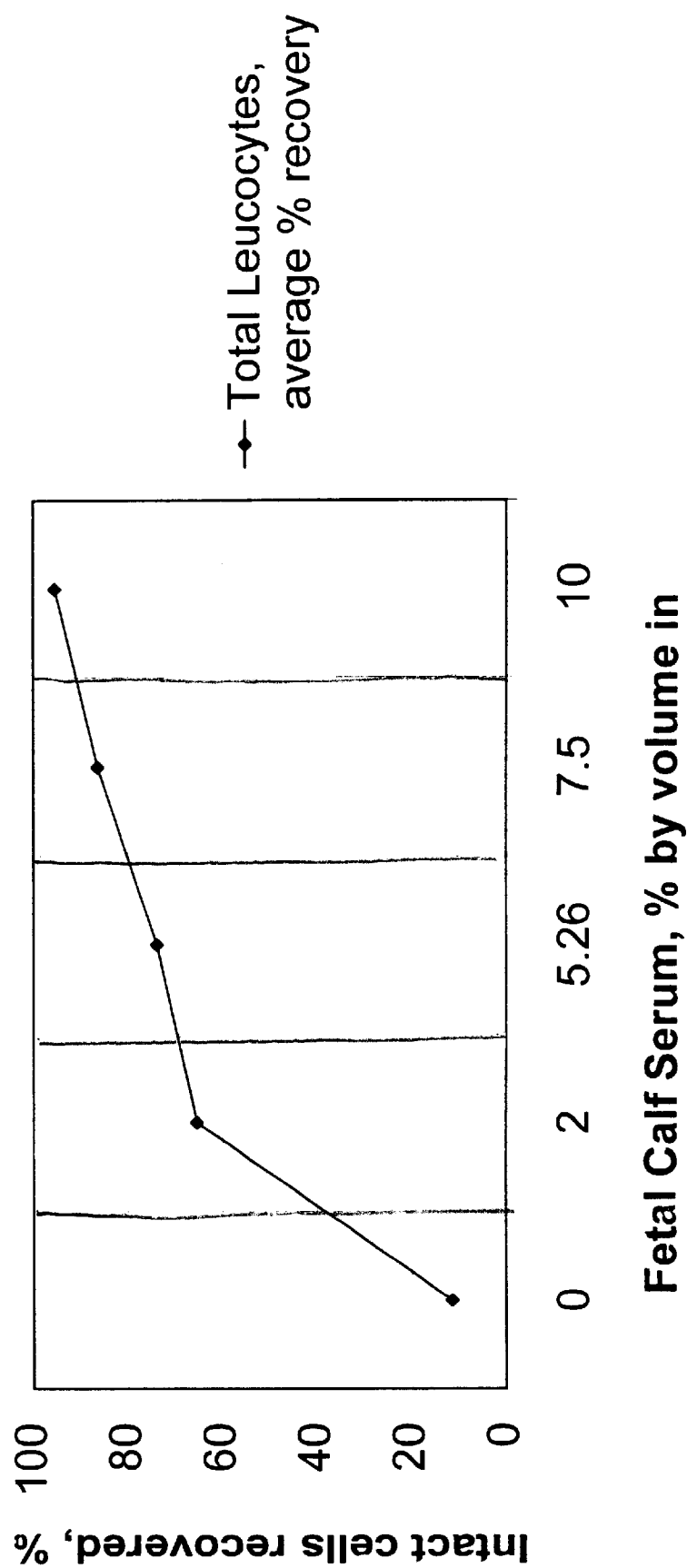

APPARATUS AND METHOD FOR SAMPLE PURIFICATION AND ANALYSIS

CROSS-REFERENCE TO RELATED APPLICATIONS

This application is a continuation-in-part of pending U.S. patent application Ser. No. 09/611,847, filed Jul. 7, 2000.

FIELD OF THE INVENTION

The invention relates generally to the field of test sample preparation and analysis. More particularly, the subject invention relates to a method and apparatus for automatically purifying a test sample and enhancing the sensitivity of the sample analysis.

BACKGROUND OF THE INVENTION

Flow cytometry is a well known technique for qualitatively and quantitatively analyzing a large number of individual cells for a specific cellular marker in a rapid manner. In a typical application, a fluorescent molecular probe that selectively binds to a predetermined cell marker, such as a fluorochrome-conjugated antibody that specifically binds an intracellular or cell surface antigen, is added to a cell sample to be analyzed so that the probe can bind or "stain" the cells within the sample that express the predetermined cell marker. The sample is then placed in flow cytometer and illuminated with a light source to enable the fluorescence associated with each cell in the sample to be quantified. The magnitude of fluorescence emitted from a particular cell correlates with the quantity of cell marker on or in that particular cell. By extrapolating this fluorescence data, the relative quantity of specific phenotypic markers expressed by cells in a sample can be rapidly and accurately determined. For an overview of flow cytometric analysis see, "Flow Cytometry and Sorting," Myron R. Melamed, Tore Lindmo, and Mortimer L. Mendelsohn, eds., New York:Wiley-Liss, Inc., (3rd ed., 1995); Shapiro, H. M., "Practical Flow Cytometry," New York:Wiley-Liss, Inc., (2nd ed., 1990).

Sample preparation for flow cytometric analysis is typically performed in a non-automated fashion, wherein a saturating concentration of a cell marker-specific probe is added to a cell sample by manual pipetting, and the mixture is then incubated for a period of time sufficient to allow the probe to bind the cell marker of interest. For analyses where red blood cells might cause interference (e.g., immunophenotyping leukocytes), the red blood cells can be removed from the sample using an agent that specifically lyses erythrocytes (for example, a hypotonic solution, ammonium chloride or carboxylic acid). Traditionally, to remove interfering unbound probe from the cell sample prior to flow cytometric analysis, the mixture is washed by adding excess buffer to the mixture, centrifuging the mixture to separate the cells from the buffer, removing the buffer containing the unbound probe, and resuspending the cells in fresh buffer. The washing procedure can be repeated multiple times to further remove any remaining unbound probe. This non-automated technique is advantageous in that it results in a relatively clean sample that contains few interferants (for example, unbound probe or cell debris) which might generate background noise or interference during the flow cytometric analysis. For many applications, however, this non-automated technique is relatively time-consuming, can result in significant cell loss due to one or more wash steps, and exposes the cells to the potentially deleterious effects (for example, activation of enzymatic processes, granule release, cell destruction, high gravity forces produced by centrifugation, etc.).

While the foregoing technique is acceptable for infrequent analyses involving a small number of samples, it is less suitable for protocols involving repeated analyses of a large number of samples. A more automated procedure is generally preferred when flow cytometric analysis is employed for clinical diagnostics, high-throughput screening, or the like. For example, in a typical clinical assay where leukocytes are immunophenotyped using flow cytometry, a sample of whole blood is placed into an apparatus that automatically processes the sample prior to analysis. One such apparatus is the COULTER® TQ-Prep™ Workstation system manufactured by Beckman Coulter, Inc. (Miami, Fla.). After adding a probe to the sample, this apparatus uses computer-controlled devices to automatically add an agent that lyses erythrocytes in the sample and a cell fixing agent (for example, paraformaldehyde). The prepared sample can then be analyzed using a flow cytometer without further processing. This automated technique is advantageous in that samples of whole blood can be prepared for analysis quickly and efficiently.

A drawback of this lysing technique can be encountered in applications requiring a high degree of sensitivity. In such applications, in the absence of a washing step, the automated technique does not remove interferants, such as unbound probe or debris from the lysed erythrocytes from the sample. The high background signal caused by the fluorescence from the unbound probe, non-specific probe binding, and/or autofluorescence from the cells and debris can obscure results generated from the analysis.

Where a fluorescently-labeled antibody is used to analyze a cell sample for a marker present in low quantities, the absence of a washing step can result in high background fluorescence caused by the unbound antibody present in the sample. Thus, if too many unbound fluorescent antibody molecules are present in the sample, the flow cytometer can not distinguish the signal emitted from the antibody-bound cells from the "noise" generated by the unbound antibody. That is, the "noise" in the sample overwhelms the "signal" emanating from the cells of interest. To avoid this, the signal to noise ratio in the sample can be improved by removing the interferants by manually washing. An example of manual washing comprises centrifuging the sample to pellet the cells, decanting the interferants contained in the supernatant, and resuspending the cells in fresh buffer. As described above for the non-automated technique, this manual washing is disadvantageous because it is time consuming, causes cell damage, and can result in significant cell loss.

A need therefore exists for an apparatus and method for quickly and efficiently removing interferants from a cell sample prior to analysis. In addition, the apparatus and method should minimize the risk of exposure to infectious blood because of operator handling of the blood cell sample. An apparatus that performs the foregoing method with only negligible cell loss, and does not expose cells to high gravitational forces or cell packing caused by centrifugation would be especially advantageous.

Similarly, there exists a need for an apparatus and method for quickly and efficiently removing interferants from a test sample prior to analysis. In addition, the apparatus and method should minimize the risk of exposure to test sample because of operator handling of the test sample. An apparatus that performs the foregoing method with only negligible loss of the composition of interest in the test sample, and does not expose test sample to high gravitational forces caused by centrifugation would be especially advantageous.

SUMMARY OF THE INVENTION

It has been discovered that filters, such as microporous hollow fiber membranes, can be utilized in sample preparation devices to quickly and efficiently remove interferants from a test sample comprising a mixture of a composition of interest and interferants. More specifically, it has been found that the use of a hollow fiber membrane having a plurality of pores with a mean diameter less than the diameter of the composition of interest can be utilized to remove interferants from a test sample containing the composition of interest and interferants to improve the signal-to-noise ratio in an assay of the composition of interest. Application of vacuum to the hollow fiber membrane permits interferants to be removed from a test sample within a lumen of the filter with little or no damage to the composition of interest. As the composition of interest does not pass through pores of the membrane, compared with conventional continuous filtration devices, clogging of the filter is less frequent, and the composition of interest is exposed to less deleterious forces. Filters within the invention can be installed in a processing apparatus such that a test sample can be washed and analyzed automatically.

Accordingly the invention features an apparatus for automatically removing interferants from a test sample containing a composition of interest and interferants. The apparatus includes a vacuum source; a filtration device comprising an impermeable housing that forms an extramembrane chamber wherein said chamber contains a filter that selective separates a composition of interest from a mixture of the composition of interest and interferants, and wherein said housing contains at least two ports, preferably more than three ports, and wherein at least one port is connected by a conduit to the vacuum source; a conduit from one of said ports in said housing which is adapted to aspirate the mixture of the composition of interest and interferants from a container into the filtration device by said vacuum source; and a conduit from one of said ports in said housing which fluidly connects to a buffer reservoir, which provides a means for buffer to enter into said filtration device and exit through one of said ports. The apparatus further includes a conduit, which is fluidly connected to an analyzer that analyzes the composition of interest by suitable means, such as an electrical measurement and optical measurement.

In a preferred embodiment, the apparatus for automatically removing interferants from a test sample containing a mixture of a composition of interest and interferants includes recovery of the composition of interest through the same conduit which is adapted to aspirate the test sample from the test sample container.

The filter of the apparatus preferably includes a microporous hollow fiber membrane having a plurality of pores sized such that the composition of interest is prevented from passing through the hollow fiber membrane. For example, the pores can have a mean diameter of between about 0.1 and 5.0 microns. In preferred versions of the apparatus, the microporous hollow fiber membrane is fashioned into at least one tube defining a lumen, the tube having a first port providing a first opening in the tube, and a second port providing a second opening in the tube. In this preferred embodiment, the conduit can be fluidly connected to the at least one lumen via the first port such that the test sample can be moved from the test sample container through the first port into the at least one lumen. The second port can be fluidly connected to a buffer reservoir containing a buffer and also fluidly connected to a detergent solution reservoir containing a detergent solution. The means for recovering the cells from the filtration device can include a fluid pump that can be in fluid communication with a buffer reservoir suitable for housing a buffer so that the fluid pump can cause the buffer to flow from the buffer reservoir into the filtration device. In variations, the fluid pump can also cause the buffer to flow from the filtration device into the at least one conduit.

In another aspect of the apparatus of the invention, the invention provides an automated method for removing interferants from a mixture of a composition of interest and interferants comprising applying a vacuum force to a first container containing a mixture of a composition of interest and interferants to cause the mixture containing the composition of interest and interferants to contact a filter; applying a force to said mixture in contact with the filter to selective separate the composition of interest from the mixture of the composition of interest and interferants; and recovering the composition of interest from the filter. Preferably the force used to enable the filter to selectively separate the composition of interest from the mixture is a vacuum force. In another aspect, the apparatus of the invention can include a computer controller for controlling the pumps and valves.

The invention also features an automated method of preparing a body fluid for analysis comprising adding at least one an analyte specific bead that reacts with a body fluid to form a test sample mixture containing an analyte specific bead complex and interferants; automatically removing interferants from said test sample mixture to yield a washed analyte specific bead complex; and analyzing the washed analyte specific bead complex to determine a characteristic of the body fluid.

The invention further features a method for purification of a proteinaceous material from a mixture of the proteinaceous material and interferants comprising supplying a first end of a hollow fiber filter with a mixture of a proteinaceous material having a molecular weight between approximately 50,000 and 1,000,000 and interferants having a molecular weight that is less than 50% of the molecular weight of the proteinaceous material to a first end of a hollow fiber filter; applying a pressure force to a lumen of the hollow fiber filter to cause the interferants in the mixture to pass through the membrane of the hollow fiber filter; adding buffer or other fluid which does not react with the proteinaceous material to further cause the interferants to pass through the membrane of the hollow fiber filter; and recovering the proteinaceous material from a second end of the hollow fiber filter, said second end being disposed at an opposite end of the hollow fiber filter from the first end. The proteinaceous material is selected from the group consisting of antibodies, activated antibodies, fluorescent labels, activated fluorescent labels, and conjugated antibody fluorescent label.

In addition, the invention even further features a method for a method for purification of a biological macromolecule from a mixture of the biological macromolecule and interferants comprising supplying a first end of a hollow fiber filter with a mixture of a biological macromolecule having a molecular weight between approximately 20,000 and 2,000,000 and interferants having a molecular weight that is less than 50% of the molecular weight of the biological macromolecule to a first end of a hollow fiber filter; applying a pressure force to a lumen of the hollow fiber filter to cause the interferants in the mixture to pass through the membrane of the hollow fiber filter; adding buffer or other fluid which does not react with the biological macromolecule to further cause the interferants to pass through the membrane of the hollow fiber filter; and recovering the biological macromolecule from a second end of the hollow fiber filter, said second end being disposed at an opposite end of the hollow fiber filter from the first end. The biological macromolecule is selected from the group consisting of nucleic acids and complex carbohydrates.

The methods further includes analyzing the composition of interest, the proteinaceous material or the biological macromolecule by suitable means, such as an electrical measurement and optical measurement.

BRIEF DESCRIPTION OF THE DRAWINGS

FIG. 14 is a graph showing the percent of intact cells recovered after three wash cycles wherein the wash buffer had increasing amounts of fetal calf serum.

DETAILED DESCRIPTION OF THE INVENTION

Figure 1:
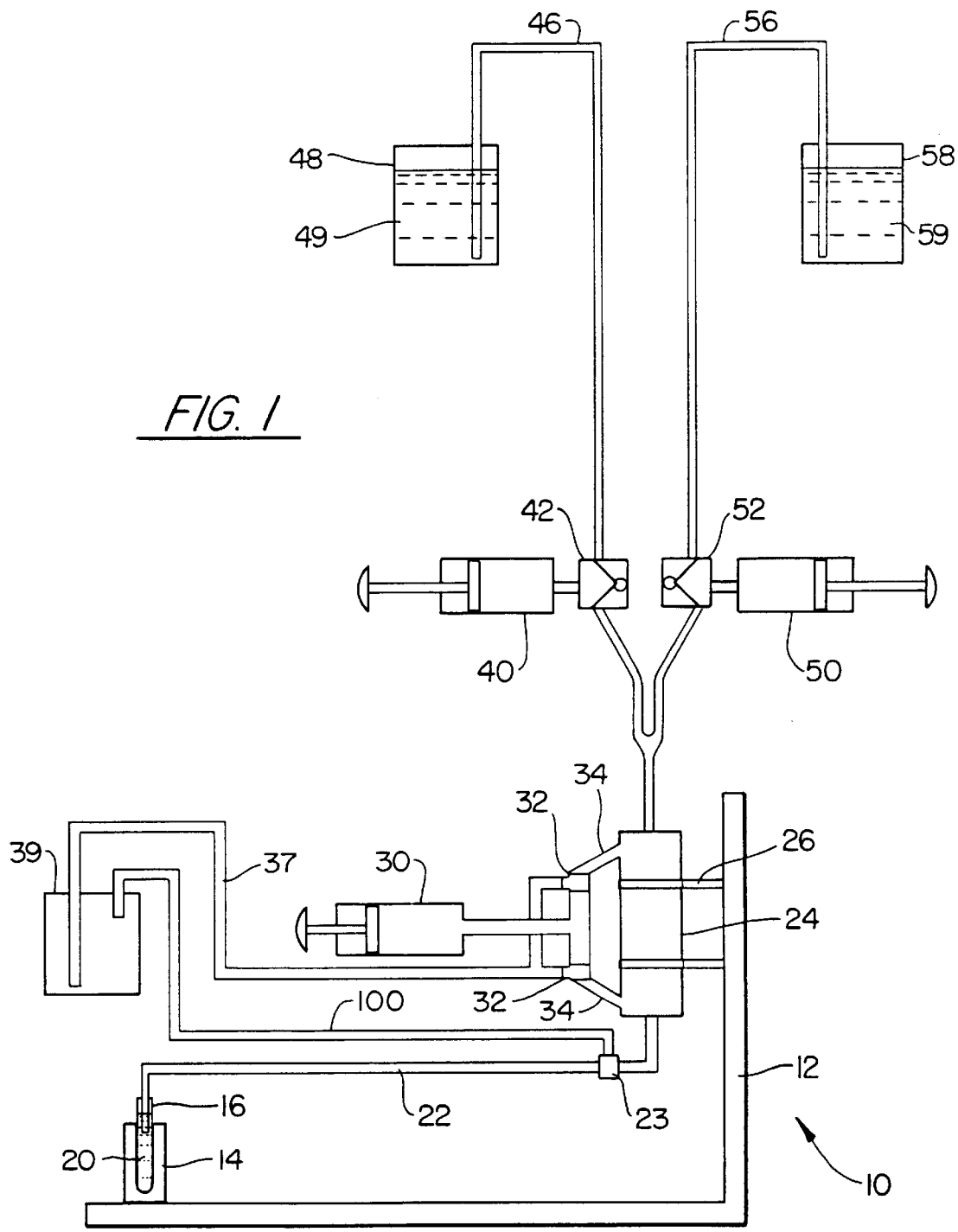
FIG. 1 is a schematic view of an apparatus within the invention.

The below described preferred embodiments illustrate various adaptations of the invention. Nonetheless, from the description of these embodiments, other aspects of the invention can be readily fashioned by making slight adjustments or modifications to the components and steps discussed below.

All publications, patent applications, patents, and other references mentioned herein are incorporated by reference in their entirety. In the case of conflict, the present specification, including definitions will control. In addition, the particular embodiments discussed below are illustrative only and not intended to be limiting.

Unless otherwise defined, all technical terms used herein have the same meaning as commonly understood by one of ordinary skill in the art to which this invention belongs.

The invention provides an automatic apparatus and automatic method utilizing a filter to remove interferants from a body fluid and reaction mixtures of body fluids prior to analysis. As used herein, "body fluids" include plasma; urine; serum; cerebral spinal fluid; bone marrow; cells; proteinaceous materials, such as antibodies and biological macromolecules from 20,000 molecular weight up to 2,000,000 mw, such as nucleic acids or complex carbohydrates. As used herein the term "automatic" means performed without direct human intervention. For example, an automatic apparatus automatically performs a method when a component of the apparatus, rather than a human operator, performs one or more steps of the method, even though a human operator might input instructions into the machine or even perform one of the steps manually. Similarly, an "automated" method is a method performed automatically. The term "interferants" means substances or particles that are undesirable. Removing the interferants from the mixture will provide a higher concentration of the composition of interest in the mixture. Typically, the interferants will obscure an analysis of the composition of interest. One limitation on the interferants is that it will be a different size from the composition of interest. More specifically, the interferants comprise non-reacted chemical agents, such as chemical substances and chemical particles; non-reacted biological agents, such as biological substances and biological particles. Typical biological particles include red blood cell debris and cellular matter smaller than the cellular matter of interest. Interferants in a cell sample analyzed fluorescently typically include unbound fluorescent probe and autofluorescent cell debris. Interferants in a mixture of a composition of interest and interferants typically include unbound fluorescent probe, autofluorescent substances or particles, and undesirable biological or chemical substances and biological or chemical particles. One example of an undesirable chemical substance includes glutaraldehyde, which is used to activate antibodies. The free glutaraldehyde impedes the conjugation of the activated antibody with other activated proteins, such as fluorochromes. A particular percentage of interferants is removed from a mixture of a composition of interest and interferants when either (a) the amount of the interferants in the mixture is decreased by that percentage or (b) the signal to noise ratio is improved by that percentage. The term "composition of interest" means a substance or particle that is desirable to be separated from a mixture comprising a composition of interest and the interferants to be removed. The composition of interest can include body fluids, biological macromolecules from 20,000 molecular weight up to 2,000,000 mw, such as nucleic acids or complex carbohydrates, as well as an analyte specific bead, such as ion sensor generally described in U.S. Pat. No. 6,165,796; metabolite sensor generally described in U.S. Pat. No. 5,747,349; and an enzyme sensor. The analyte specific beads typically has a size of from approximately 1 to 20 microns. More particularly, the analyte specific bead comprises a bead attached to a ligand binding element, such as a antibody. When using the analyte specific bead, the ligand binding element will attach to the analyte. In a further process, the analyte specific bead attached to the analyte is further attached with another ligand binding element which contains a detection element, such as a fluorescent dye.

Referring to FIG. 1 of the drawings, a presently preferred embodiment of a cell wash apparatus 10 includes a sample container holder 14 and a filtration device 24 mounted to a frame 12. Sample container holder 14 accommodates a sample container 16 containing a sample of cells 20 in an arrangement such that an end of a sample hose 22 can be inserted into the sample of cells 20 which can contain interferants. Sample hose 22 is fluidly connected to vacuum source 30 so that actuation of vacuum source 30 supplies a vacuum force which aspirates the sample of cells 20 from sample container 16 into hose 22. More specifically, there is an absence of air in filtration device 24 such that when vacuum force 30 is applied, the cell sample 20 is aspirated form the sample container 16 into the filtration device 24.

Vacuum source 30 can take the form of any device that can provide a vacuum or hydraulic force for moving fluids. For example, vacuum source 30 can be a fluid pump or an external vacuum line. Preferably, the vacuum source 30 is a syringe pump, for example a 5 ml syringe pump, that can provide a vacuum to filtration device 24 when its plunger is withdrawn and a forward hydraulic force when its plunger is depressed.

Devices that cause a vacuum force rather than a positive pressure are the preferred form of source 30, because it has been found that a vacuum is less damaging to cells. More specifically, the sample of blood cells 20 does not circulate through a pump to enter into the lumen 66 (not shown). If the cells circulate through a pump, then cell deformation, aggregation and deterioration occur. Therefore, the sample of cells 20 enter the lumen 66 by action of a vacuum force rather than by the action of a force which is applied to the sample of blood cells 20 which cause the sample of cells 20 to be pushed into the lumen 66.

Filtration device 24 is attached to frame 12 by a filtration device fastener 26 and interposed between sample hose 22 and vacuum source 30 so that application of a vacuum by vacuum source 30 causes aspiration of sample of cells 20 into filtration device 24. Filtration device 24 can be any device that can remove interferants such as unbound antibody molecules or cellular debris from sample of cells 20. In a preferred embodiment, filtration device 24 includes a filter through which interferants can pass. Filters that can be used include fine mesh screens, flat microfiltration membranes, spiral wound membrane cartridges, or any other media that can separate interferants from the cells of interest. In a more preferred embodiment, the filter is a microporous hollow fiber membrane that has a plurality of pores sized less than the blood cells within sample of cells 20 but greater than the interferants.

Suitable hollow fiber membranes for use as filtration device 24 can be fashioned by one of skill in the art or can be purchased from a variety of commercial sources. Hollow fiber membranes useful in the invention comprise a material which is non reactive with the cells of interest and can be a hydrophobic or hydrophilic material, polysulfone, polyestersulfone, nylon, methylacrylates, Peek™ (Upchurch Scientific, Inc.). The filter will have pores sized so that cells of interest cannot pass therethrough. The pore size will range from approximately 0.1 microns to about 5 microns in diameter. Preferably, the pore size will range from approximately 0.1 microns to about 3 microns, which can eliminate platelets as interferants from the cells of interest. More preferably, the pore size will range from approximately 0.2 microns to about 2 microns and most preferably the pore size will range from approximately 0.3 microns to about 1 micron. In the present invention, a pore size of about 0.65 microns has been successfully used to eliminate interferants leaving a majority of cellular components for analysis. One preferred commercially available polysulfone hollow fiber membrane device having a plurality of pores with a mean diameter of 0.65 microns is sold as Catalog # CFP-6-D-H22LA by A/G Technology Corporation (Needham, Mass.). This device is suitable for removing the majority of interferants from a typical sample of 100 microliter of whole human blood that has been stained with a fluorescent antibody, erythrocyte-lysed, and diluted to a total volume of about 4 ml using an isotonic buffer or reagent. Other devices useful for variations of the invention include CFP-6-D-MB01 (15 $cm^2$), and CFP-6-D-MM01A (24 $cm^2$) from A/G Technology Corporation; and X15E300 04N and X25E201 02N from Spectrum Laboratories, Inc. (Rancho Dominguez, Calif.).

A sample hose valve 23 for regulating fluid flow between sample container 16 and filtration device 24 is positioned on hose 22. Valve 23 can take the form of any device that can control the flow of fluid through hose 22. Preferably, valve 23 is switchable between an open position and a closed position. In the open position, sample 20 can flow between container 16 and filtration device 24 when a suitable force is applied, such as by vacuum source 30. In the closed position, the fluid connection is blocked so that sample 20 cannot flow between container 16 and filtration device 24. In a preferred variation of the foregoing, valve 23 also has a partially open position that directs fluid flow from hose 22 to a waste reservoir 39 by another fluid connection.

Although in the embodiment shown in FIG. 1 the fluid connection between sample container 16 and filtration device 24 is provided by sample hose 22 and regulated by valve 23, in an alternate preferred embodiment, more than one fluid connection can exist between sample container 16 and filtration device 24. For example, sample hose 22 can be utilized for transporting sample of cells 20 from container 16 to filtration device 24 and a return hose or fluid connector can be provided for returning sample of cells 20 from device 24 to sample container 16. A fluid flow regulator analogous to valve 23 can be interposed in the return hose. In addition, rather than having a fluid connection for returning sample 20 from device 24 to sample container 16, the apparatus can feature another pathway for transporting sample 20 from device 24 to a clean sample container, such as an unused test tube, rather than sample container 16.

Referring again to FIG. 1, vacuum source valves 32 are positioned within the fluid connection between vacuum source 30 and filtration device 24 so that they can control transfer of vacuum between vacuum source 30 and filtration device 24. Valves 32 are preferably switchable between an open and a closed position. In the open position, actuation of vacuum source 30 causes a vacuum force to be applied to filtration device 24. The vacuum will cause aspiration of sample 20 from container 16 into device 24. In the closed position, no force is transmitted between vacuum source 30 and device 24.

Vacuum source 30 can also be fluidly connected to a waste reservoir 39 by a waste hose 37. As indicated above, vacuum source 30 is also adapted to provide a forward hydraulic force. This hydraulic force can be used to move fluid from locations proximal to vacuum source 30 to waste reservoir 39. For example, when vacuum source 30 takes the preferred form of a syringe pump, with valves 32 and 23 open, withdrawal of the plunger of the syringe pump causes a vacuum that aspirates a liquid which contains interferants and sample of cells 20 to be dispersed into the interior of the syringe's barrel. Depressing the plunger at this point forcibly expels the liquid from the syringe. With valves 32 closed, the liquid is directed through waste hose 37 into waste reservoir 39. In an alternative variation of the foregoing, rather than using vacuum source 30, an additional vacuum source, pump, or hydraulic force transducer can be utilized to move fluid from locations proximal to vacuum source 30 to waste reservoir 39. This latter variation is preferred where it is desired to avoid potential cross contamination between waste reservoir 39 and sample container 16 and their associated fluid connections.

Filtration device 24 can also be fluidly connected to buffer reservoir 48 by buffer hose 46. Buffer reservoir 48 is a container for housing buffer 49 which can be any isotonic solution compatible with sample of cells 20. Suitable buffers include physiological saline or phosphate buffered saline (PBS) and Hanks Buffer. Preferred isotonic solutions for use as buffer 49 include IsoFlow™ buffer, PBS, and IMMUNOTROL® Final Storage buffer (all available from Beckman Coulter, Inc., Miami, Fla.).

Interposed between device 24 and reservoir 48, and fluidly communicating with hose 46 is buffer pump 40. Buffer pump 40 supplies an hydraulic force which moves buffer 49 from reservoir 48 through hose 46, filtration device 24, and sample hose 22 into sample container 16. Pump 40 can take the form of any device that can cause a hydraulic force between buffer reservoir 48, device 24, and sample container 16. For example it can be a vacuum pump, peristaltic pump, reciprocating pump, or other type of pump known to those skilled in the art. In preferred embodiments, however, it is a syringe pump.

Positioned on hose 46 between reservoir 48 and device 24 is a buffer valve 42 for controlling flow of buffer between reservoir 48 and device 24. Although it can be any fluid flow regulating device, valve 42 is preferably a three position stopcock-like valve that can be placed in either a fill position, a dispense position, or a closed position. In the fill position, pump 40 is in fluid connection with buffer reservoir 48 such that it can transmit an hydraulic force to hose 46 that causes pump 40 to aspirate buffer 49 from buffer reservoir 48 into buffer hose 46 or into the chamber of the syringe when pump 40 is a syringe pump. In the dispense position, pump 40 is in fluid communication with device 24 such that actuation of pump 40, for example depressing the plunger of the syringe, causes buffer 49 to be transported from pump 40 to device 24 and, where valve 23 is open, into sample container 16. Thus, referring to FIG. 1, with valve 42 in the open position, valves 32 in the closed position and valve 23 in the open position, actuation of pump 40 can cause buffer 49 to flush sample of blood cells 20 positioned within filtration device 24 back into sample container 16. With valve 42 in the closed position, the fluid connection between reservoir 48, device 24, and container 16 is blocked.

Detergent solution reservoir 58 is fluidly connected to filtration device 24 by detergent solution hose 56. Detergent solution reservoir 58 is a container for housing a detergent solution 59 which is suitable for cleaning filtration device 24 and the fluid connections of apparatus 10. Detergent solution 59 can be any solution that can remove residual samples, accumulated deposits, proteins, nucleic acids and the like from the fluid connections of apparatus 10. For example, detergent solution can be 0.5N NaOH solution, 1 N KOH solution, $H_3PO_4$ solution, 0.05–10% bleach solution, or a similar solution. The detergent solution can include substances such as Triton X-100 (Rohm and Haas), Tween 80® (ICI America), pluronic acids (BASF Corp.), ethylenediamine tetraacetic acid (EDTA), proteases, nucleases, azide, and other substances which can clean fluid connections. One preferred composition for use as detergent solution 59 is the solution sold under the trade name COULTER CLENZ® (Beckman Coulter, Inc., Fullerton, Calif.).

Detergent solution pump 50 supplies a hydraulic force which moves detergent solution 59 from reservoir 58 through hose 56 into filtration device 24. Similar to pump 40, pump 50 can take the form of any device that can cause an hydraulic force between detergent solution reservoir 58 and device 24. For example it can be a vacuum pump, peristaltic pump, reciprocating pump or other type of pump known to those skilled in the art. In preferred embodiments, however, it is a syringe pump.

Positioned on hose 56 between detergent solution pump 50 and buffer hose 56 is a detergent solution valve 52 for controlling flow of detergent solution 59 between reservoir 58 and device 24. As with valve 42, although it can be any suitable fluid flow regulating device, valve 52 is preferably a three position stopcock-like valve that can be placed in either a fill position, a dispense position, or a closed position. In the fill position, detergent solution pump 50 is in fluid connection with detergent solution reservoir 58 such that it can transmit a hydraulic force to hose 56 that causes pump 50 to aspirate detergent solution 59 from detergent solution reservoir 58 into detergent hose 56 or into the chamber of the syringe when pump 50 is a syringe pump. In the dispense position, pump 50 is in fluid communication with device 24 such that when valve 32 is closed and valve 23 is open, actuation of pump 50, for example depressing the plunger of the syringe, causes detergent solution 59 to be transported from pump 50 to device 24. And when valves 32 are in the open position and valve 23 in the closed position, actuation of pump 50, with or without the cooperation of vacuum source 30, can cause detergent solution 59 to wash any fluid or material within filtration device 24 into waste reservoir 39. With valve 52 in the closed position, the fluid connection between reservoir 58 and device 24 is blocked.

In addition to the above-described buffer and detergent solution devices, other devices can be included within apparatus 10. For example, devices for adding an erythrocyte lysing agent can be included. Similarly, devices for adding one or more cell marker probes, such as fluorescently-labeled antigen-specific antibodies, can be included within apparatus 10. In addition, fluid connections to one or more cell analyzers, such as hematology and flow cytometry analyzers, can also be provided. Thus, the invention can include an apparatus that can automatically process a sample of whole blood by lysing the red blood cells within the blood cell sample, adding a cell marker probe to the blood cell sample, removing the lysed red blood cell debris and unbound cell marker probe from the blood cell sample, and quantifying the remaining cells and quantifying specific cell markers using a cell analyzer.

In a preferred embodiment, the various components of the apparatus are controlled by an information processing unit, such as a computer. That is valves 23, 32, 42, and 52, and vacuum source 30 and pumps 40 and 50 are operatively connected to an information processing unit (not shown in the drawings) having programmed therein operating algorithms for switching the valves and actuating the pumps and vacuum sources. The information processing unit can be connected to electrical, hydraulic, or mechanical manipulators such as servos, robotic arms, gears and the like to operate the pumps, valves, and vacuum source as well as other components of apparatus 10. For example, in one embodiment, hose 22 can be attached to a robotic arm that can move hose 22 between sample container 16 and a different site, for example where another container is located, according to instructions provided by the information processing unit.

Figure 2:
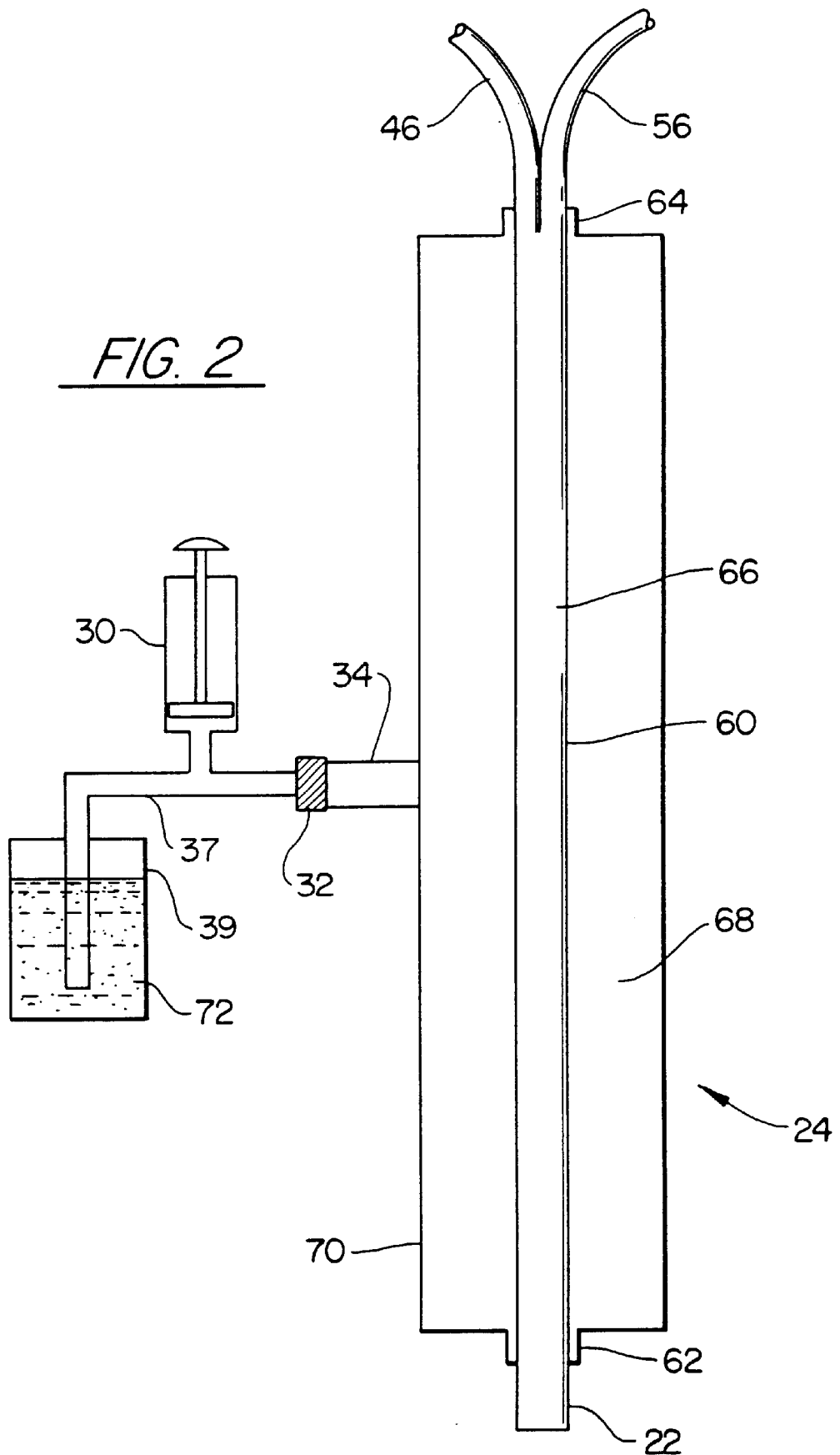
FIG. 2 is a schematic view of a filtration device within the invention.

Referring now to FIG. 2, a particularly preferred embodiment of filtration device 24 is shown in further detail. In this preferred embodiment of the apparatus of the invention, filtration device 24 includes a hollow fiber membrane 60 fashioned into a tube having a wall that defines a lumen 66. The filtration device 24 further includes a bottom port 62, which is longitudinal to the filtration device, so that tubular shaped membrane 60 fluidly connects sample hose 22 and lumen 66. Fluids, such as sample of cells 20, can enter lumen 66 from sample hose 22 by port 62. Filtration device 24 also includes a top port 64, which is longitudinal to the filtration device, so that tubular shaped membrane 60 fluidly connects hoses 46 and 56 to lumen 66. Buffer 49 (not shown) can enter lumen 66 from buffer hose 46 by port 64. Likewise, detergent solution 59 (not shown) can enter lumen 66 from detergent solution hose 56 by port 64.

Although the devices in FIGS. 2, 3 and 4A–K show only one membrane 60. In another preferred embodiment, device 24 can include more than 1 membrane 60 which forms more than 1 lumen 66. More specifically, the filtration device can have 2 membranes each forming a lumen so that the filtration device contains 2 lumens. More preferably, the filtration device contains three membranes which form 3 lumens. Most preferably, the filtration device contains four membranes which form 4 lumens. It has been found having more than 1 lumen will increase the processing flow rate. In addition, having more than 1 lumen will have less fouling and require less cleaning cycles. However, it is also preferred that the filtration device contains less than 20 membranes which form less than 20 lumens, and most preferred that it contains less than 10 membranes which form less than 10 lumens.

As noted in FIG. 2, the outer surface of filtration device 24 preferably includes a non-reactive impermeable housing 70 which envelopes hollow fiber membrane 60 and extramembrane chamber 68. The extramembrane chamber 68 is defined as the space between the inner wall of housing 70 and the outer wall of tubular membrane 60. Vacuum and waste port 34, which can be lateral to the filtration device 24, is an opening that fluidly connects extra membrane chamber 68 to vacuum source 30 and waste hose 37. Port 34 can thus project through the wall of impermeable housing 70, such that application of a vacuum force to port 34, for example from source 30, transfers the vacuum force to extramembrane chamber 68. Vacuum in chamber 68 causes fluid and interferants 72 to be withdrawn from lumen 66 across membrane 60 into chamber 68 and out through port 34. After closing valves 32 and applying a forward hydraulic force from source 30, the withdrawn fluid and interferants 72 can be transported to waste reservoir 39.

Device 24 is preferably arranged such that fluid and interferants can be withdrawn throughout the entire portion of membrane 60 contained within housing 70. For example, port 34 is preferably positioned on the device such that a vacuum from vacuum source 30 is directed approximately perpendicular with respect to the length of membrane 60. Application of a vacuum in such a crosswise manner is preferred as compression of cells is reduced compared to devices that force cells to one end of membrane 60, which occurs when a pump is used to increase pressure within the lumen of membrane 60 to expel cells through the pores of the membrane.

Figure 3:
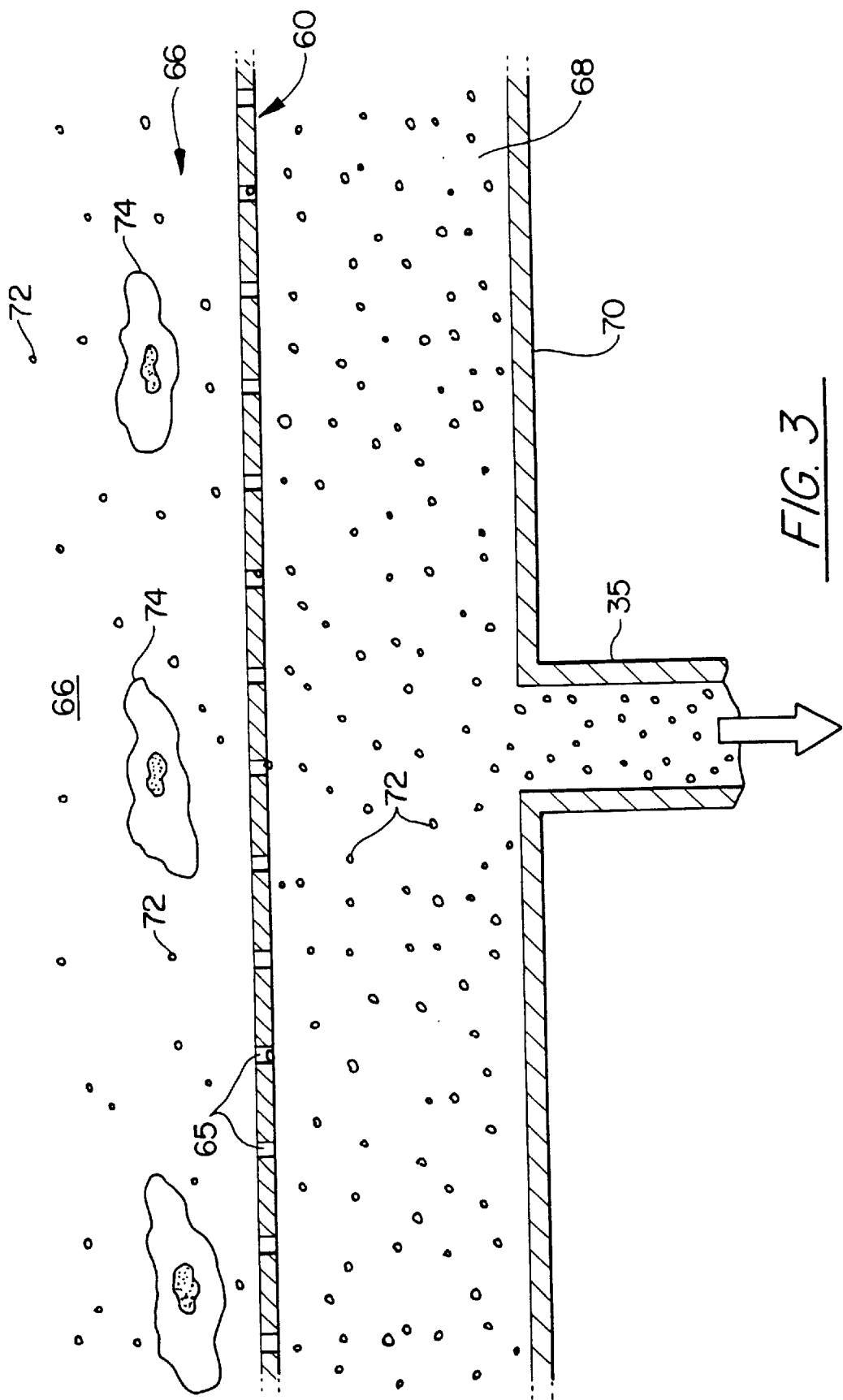
FIG. 3 is a cross-sectional view of the filtration device of the invention shown with interferants removed from a sample of cells within a lumen of a hollow fiber membrane of a filtration device.

A preferred mechanism by which filtration device 24 selectively retains the cells of interest while allowing the interferants to pass through is illustrated in FIG. 3. Sample of cells 20 is shown in lumen 66 as a mixture comprising cells 74 and interferants 72, such as unbound probe and cellular debris, which is dispersed in a liquid medium. Hollow fiber membrane 60 is shown as having a plurality of pores 65 having a mean diameter of less than the mean diameter of cells 74 but greater than the diameter of interferants 72. Interferants 72 can thus pass through pores 65 while the larger diameter cells 74 cannot. Application of a vacuum to chamber 68, through port 34, causes the liquid in which sample of cells 20 is dispersed to be withdrawn through pores 65 into chamber 68 along with interferants 72 contained within the liquid. Cells 74, being too large to pass through pores 65, are selectively retained in lumen 66.

In the embodiment shown in FIG. 3, membrane 60 can be composed of any suitable material. For example, it can be composed of a hydrophobic or hydrophilic polymer. In one preferred version it is composed of microporous polysulfone. Suitable sizes of pores 65 of membrane 60 can be selected by one of skill in the art depending on the particular characteristics of the cell sample to be analyzed. For applications where human leukocytes are analyzed, pores 65 preferably have a mean diameter of between about 0.2 and 2.0 microns, and more preferably have a mean diameter of about 0.3 microns to about 1 micron. The surface area of the membrane 60 can also be selected by one of skill in the art depending on such factors as the particular characteristics of the sample to be analyzed, the sample volume, and the type of membrane used. For example, for a 100 microliter sample of a whole human blood processed and then diluted to a total volume of about 4 ml using an isotonic buffer, 20 cm$^2$ of a hollow fiber membrane with 0.65 micron diameter pores is sufficient to remove the majority of interferants in the sample. For a 1 ml sample, preferred lumen volumes range from about 50 µl to about 2500 µl and preferably about 200 pi to about 1000 µl, and preferred extramembrane chamber volumes range from about 100 µl to about 2500 µl and preferably about 500 µl to about 1000 µl. Other lumen and extramembrane chamber volumes can be preferred depending on the volume and types of sample. Membrane 60 can also be treated with non-lytic surfactants such as Pluronic F68 and Pluronic 25R8 (BASF Corp.) to enhance its reusability without having a material adverse effect on cell count or cell marker density on cells in sample 20.

Figure 4A:
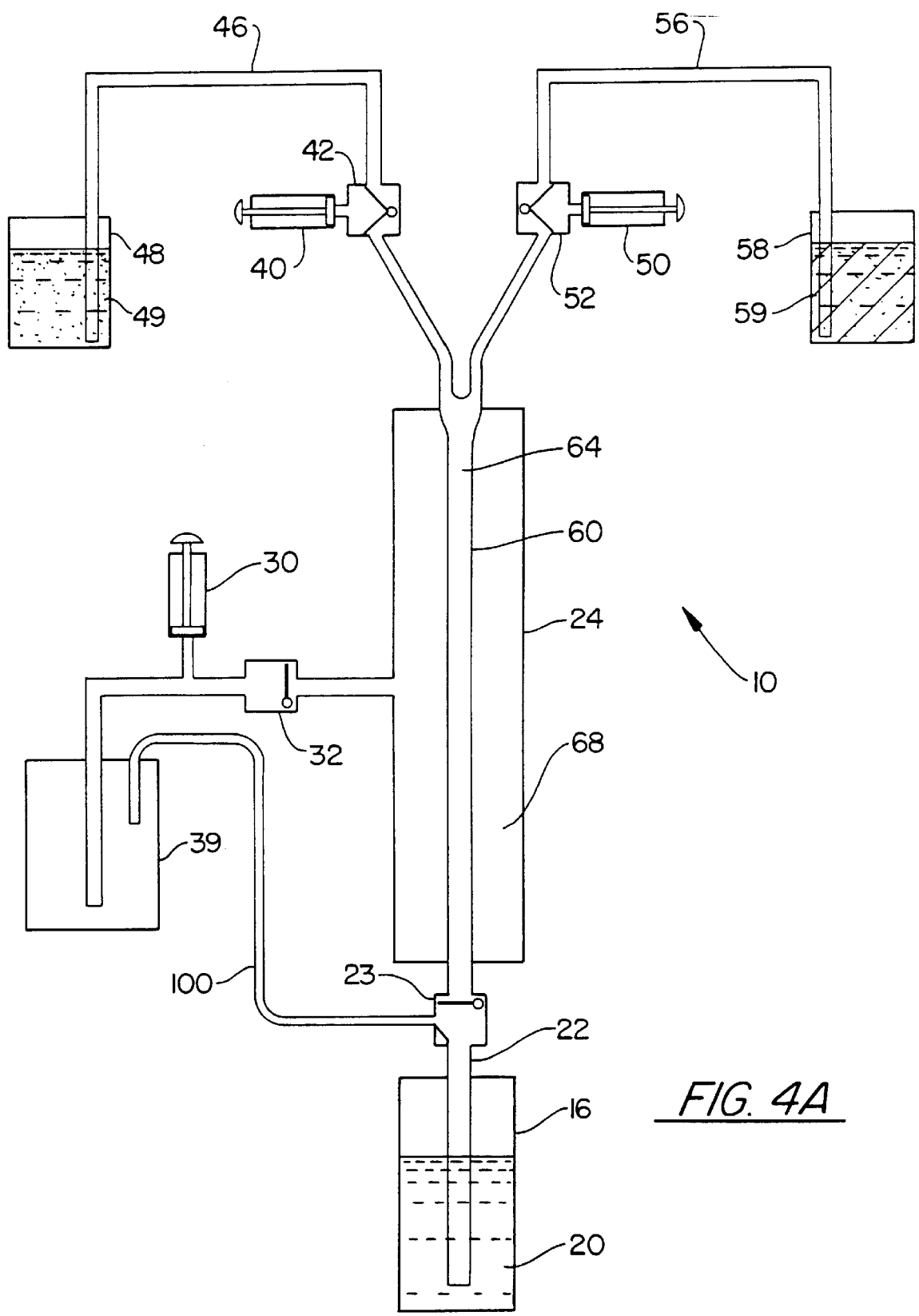
FIGS. 4A–4K are schematic views illustrating the operation of an apparatus of the invention.
Figure 4B:
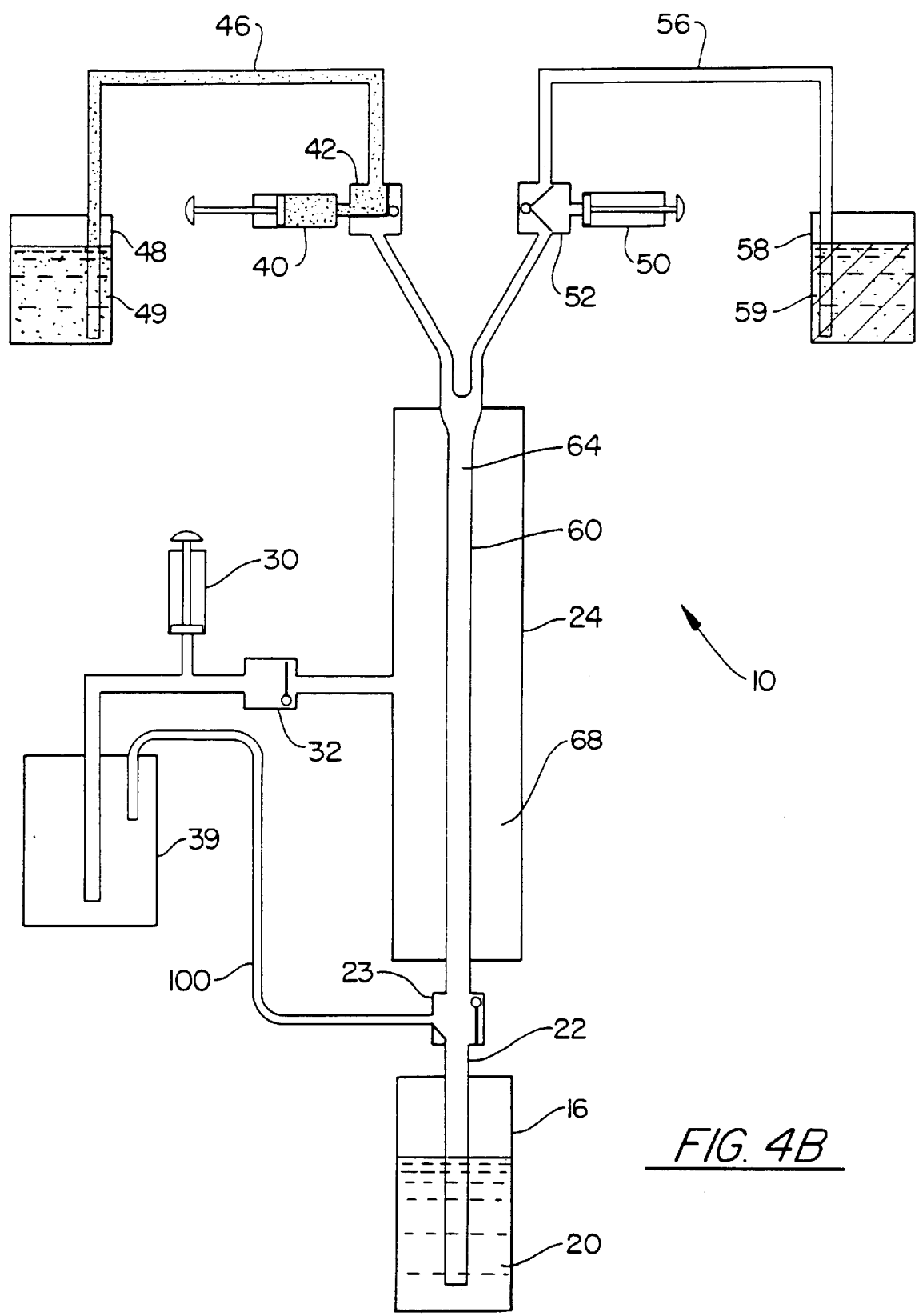
Figure 4C:
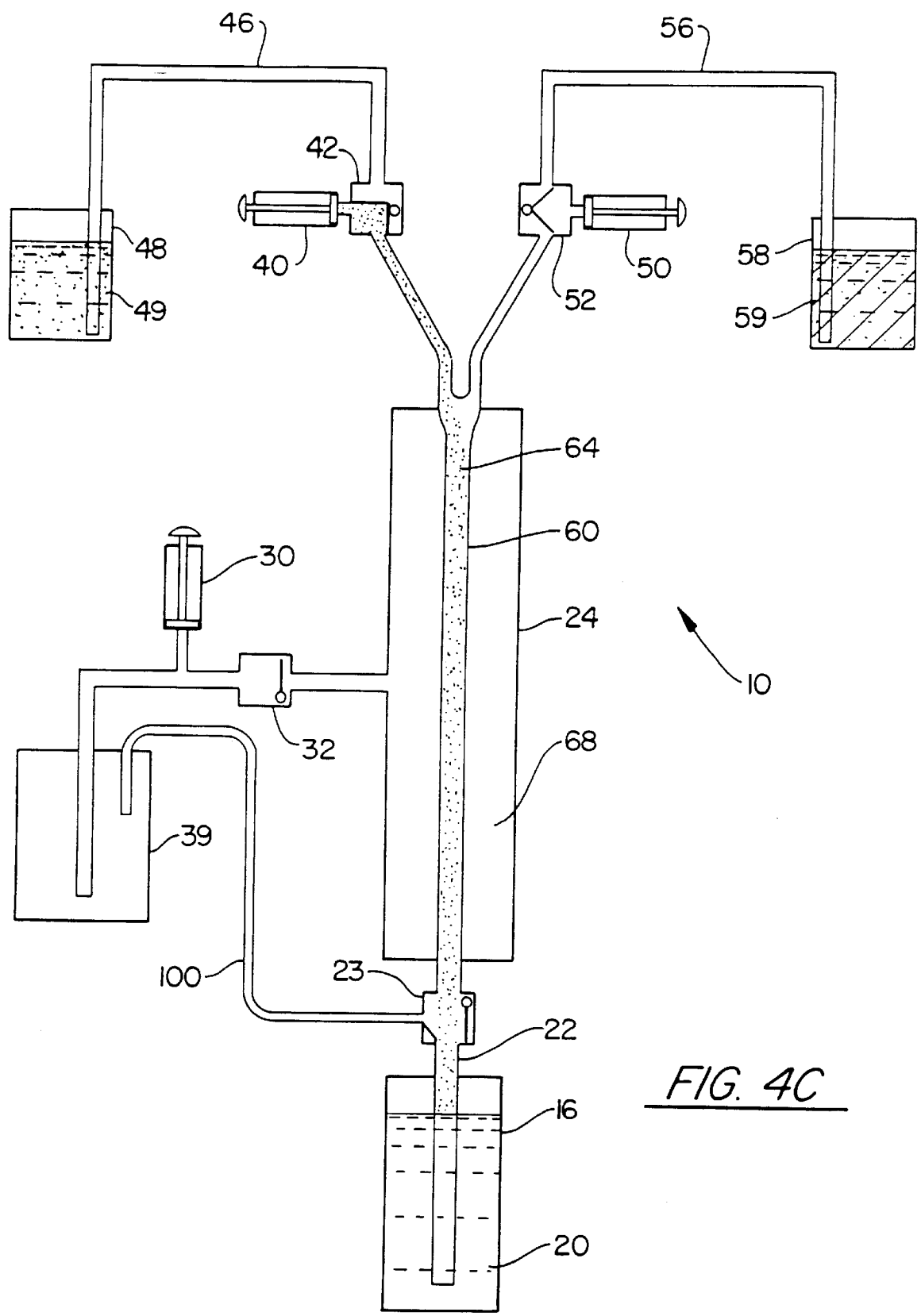

An overview of a preferred operation of an apparatus of the invention is shown in FIGS. 4A–4E. In FIG. 4A, apparatus 10 is shown with sample hose 22 in fluid communication with sample of cells 20. For example, the sample of cells 20 can be 100 µl of whole blood having been processed using a lysing reagent, a stabilizing buffer, and a fixative such as IMMUNOPREP™ reagents (manufactured by Beckman Coulter, Inc., Miami, Fla.). As illustrated in FIGS. 4B and C, sample 20 is diluted with buffer 49 to facilitate removing a greater percentage of interferants 72. To transfer a predetermined volume of buffer 49, such as to bring the total volume of the sample to about 4 ml, from buffer reservoir 48 into sample container 16, apparatus 10 is arranged by a computer control mechanism (not shown), so that valve 23 is open, and valves 32 and 52 are closed. As shown in FIG. 4B, buffer valve 42 is then switched to the fill position and buffer pump 40 is activated to aspirate the predetermined volume of buffer 49. As indicated in FIG. 4C, valve 42 is then switched to the dispense position and pump 40 is activated to dispense the aspirated volume of buffer 49 through filtration device 24 into sample container 16 thereby diluting sample of cells 20.

Figure 4D:
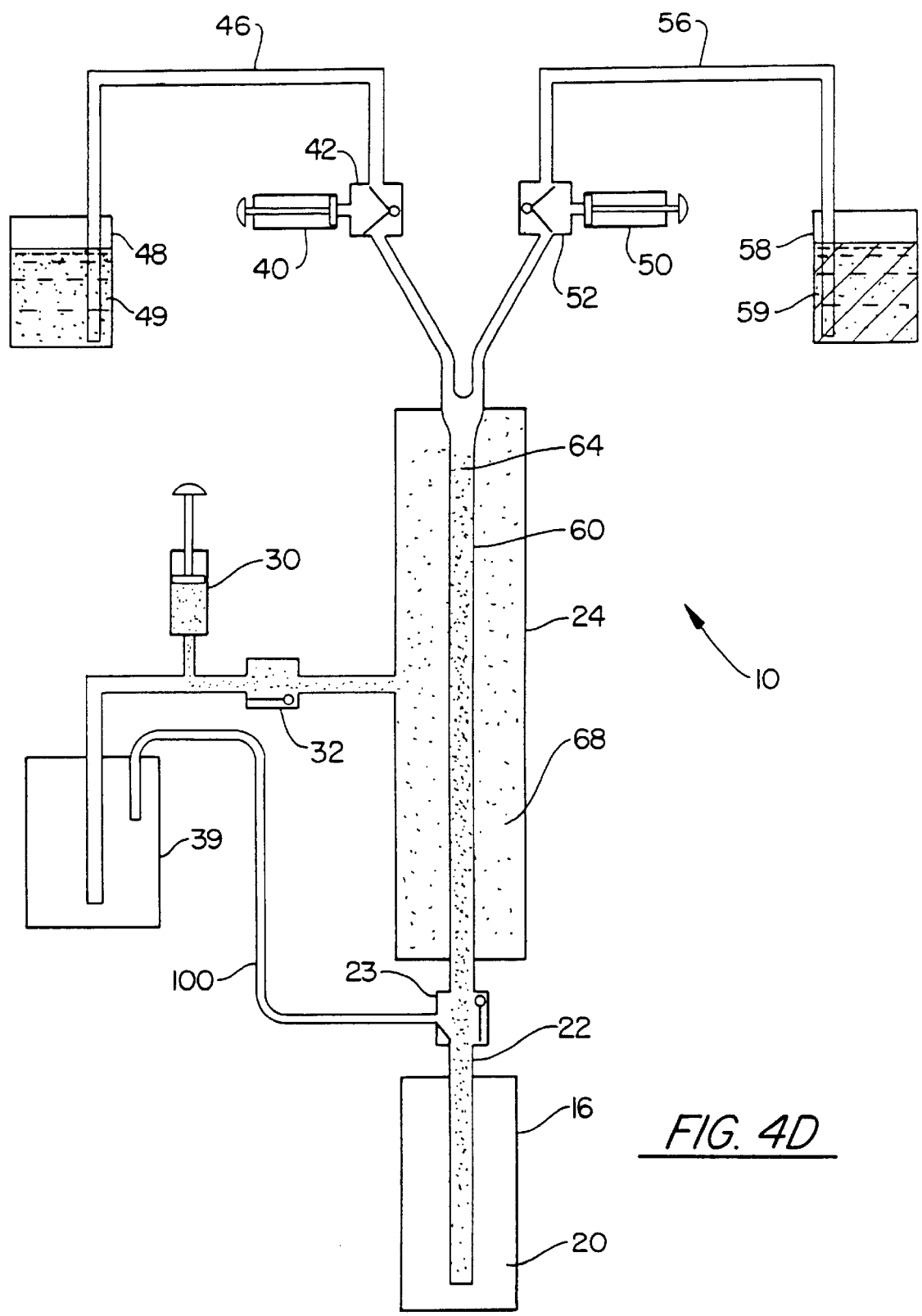
Figure 4E:
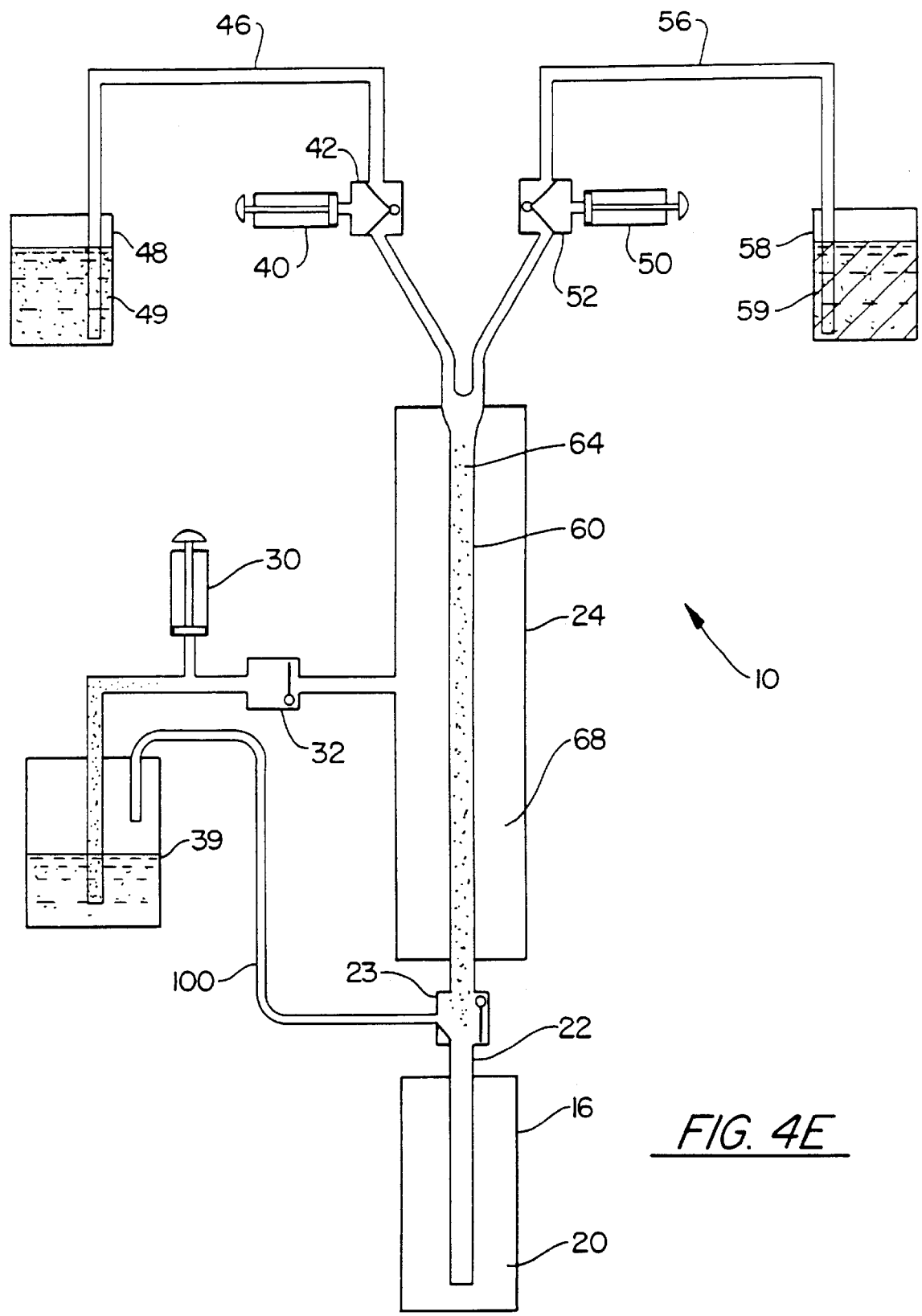

As shown in FIG. 4D, sample 20 is then aspirated into filtration device 24 where interferants are removed from the sample by having them pass through membrane 60. In this step, apparatus 10 is configured so that valves 42 and 52 are closed, and valves 23 and 32 are open. Vacuum source 30 is then activated to produce a vacuum to aspirate sample of cells 20 from container 16 into filtration device 24. While the vacuum is being supplied, the liquid in sample 20 that contains interferants is passed through device 24 into vacuum source 30, while cells are retained in device 24, within lumen 66. As shown in FIG. 4E, valves 32 are then closed and vacuum source 30 is activated to provide a forward hydraulic force to expel the aspirated liquid through waste hose into waste reservoir 39.

Figure 4F:
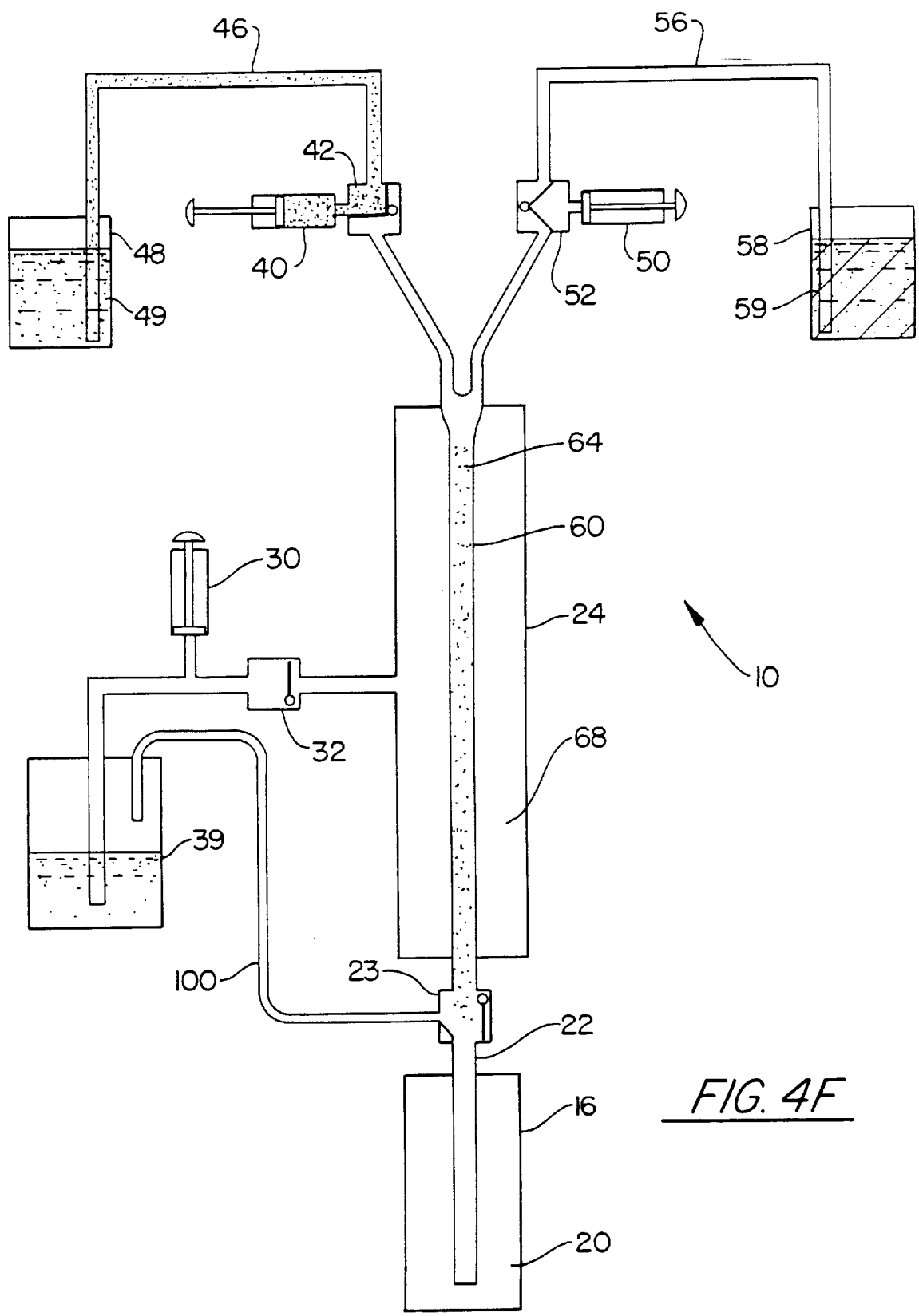
Figure 4G:
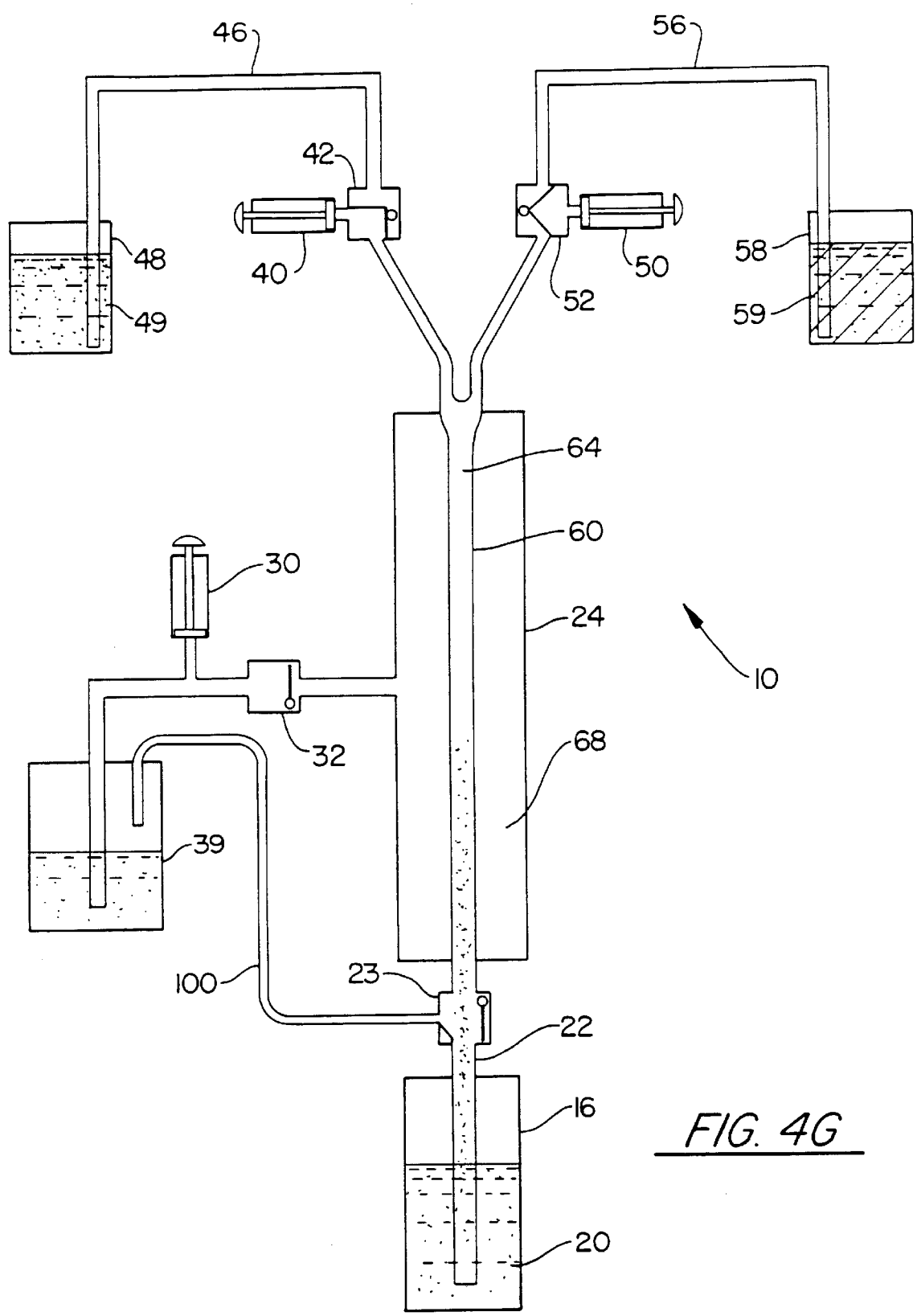

As illustrated in FIGS. 4F and G, sample of cells 20 from which interferants have been removed is then transferred back into container 16. In this step, apparatus 10 is configured so that valve 23 is open, and valves 32 and 52 are closed. In FIG. 4F, buffer valve 42 is then switched to the fill position and buffer pump 40 is activated to aspirate a predetermined volume of buffer 49, for example 1.25 ml, from buffer reservoir 48. Valve 42 is then switched to the dispense position and pump 40 is activated to dispense the aspirated volume of buffer 49 through filtration device 24 into sample container 16 as illustrated in FIG. 4G. Movement of buffer 49 through device 24 flushes sample of cells 20 from the device into container 16. In an alternative embodiment (not shown), an additional fluid connection from device 24 to a clean sample container rather than sample container 16 can be provided, such that after the interferants have been removed from sample of cells 20, the sample can be transported from device 24 to the clean container.

Figure 4H:
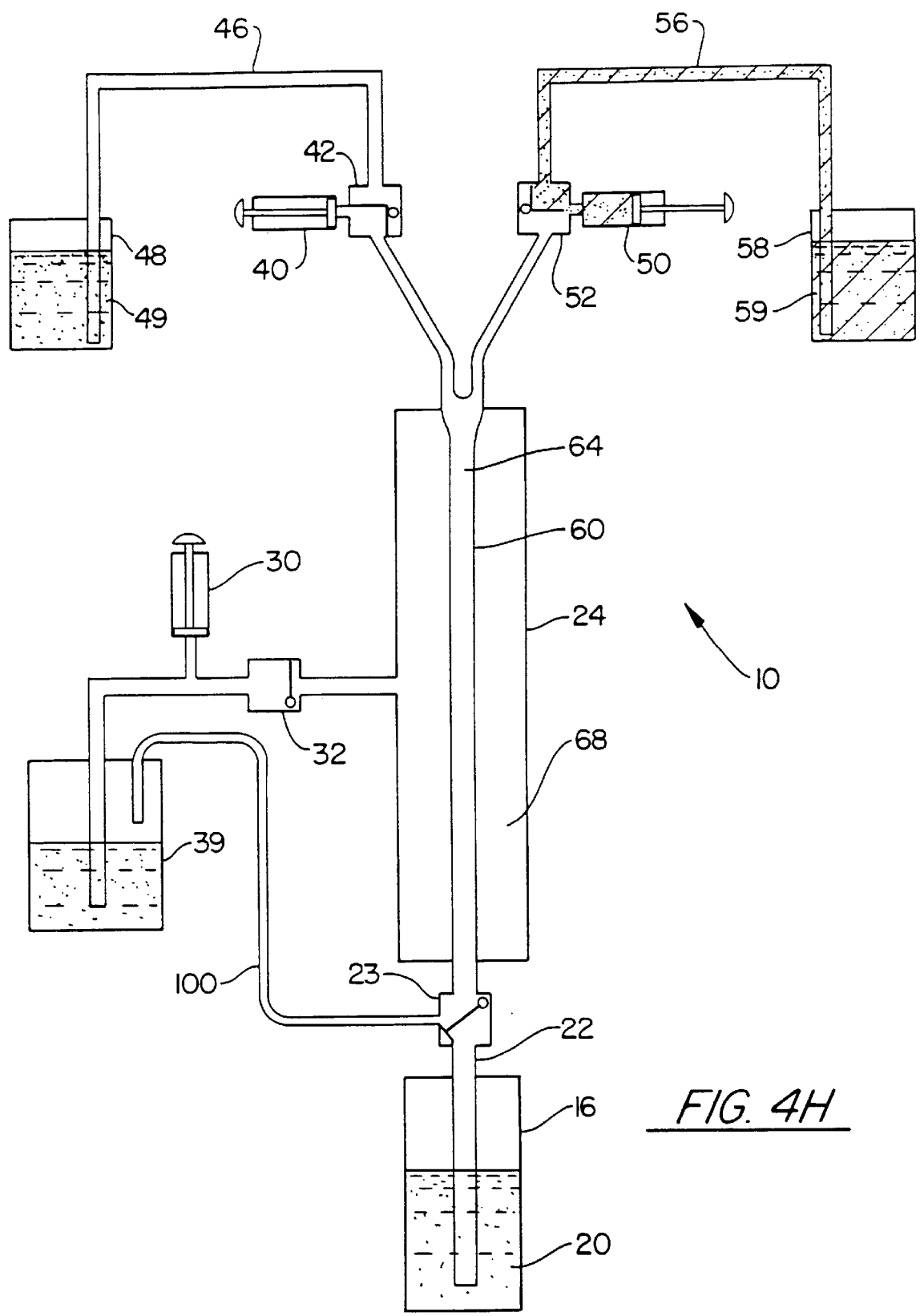
Figure 4I:
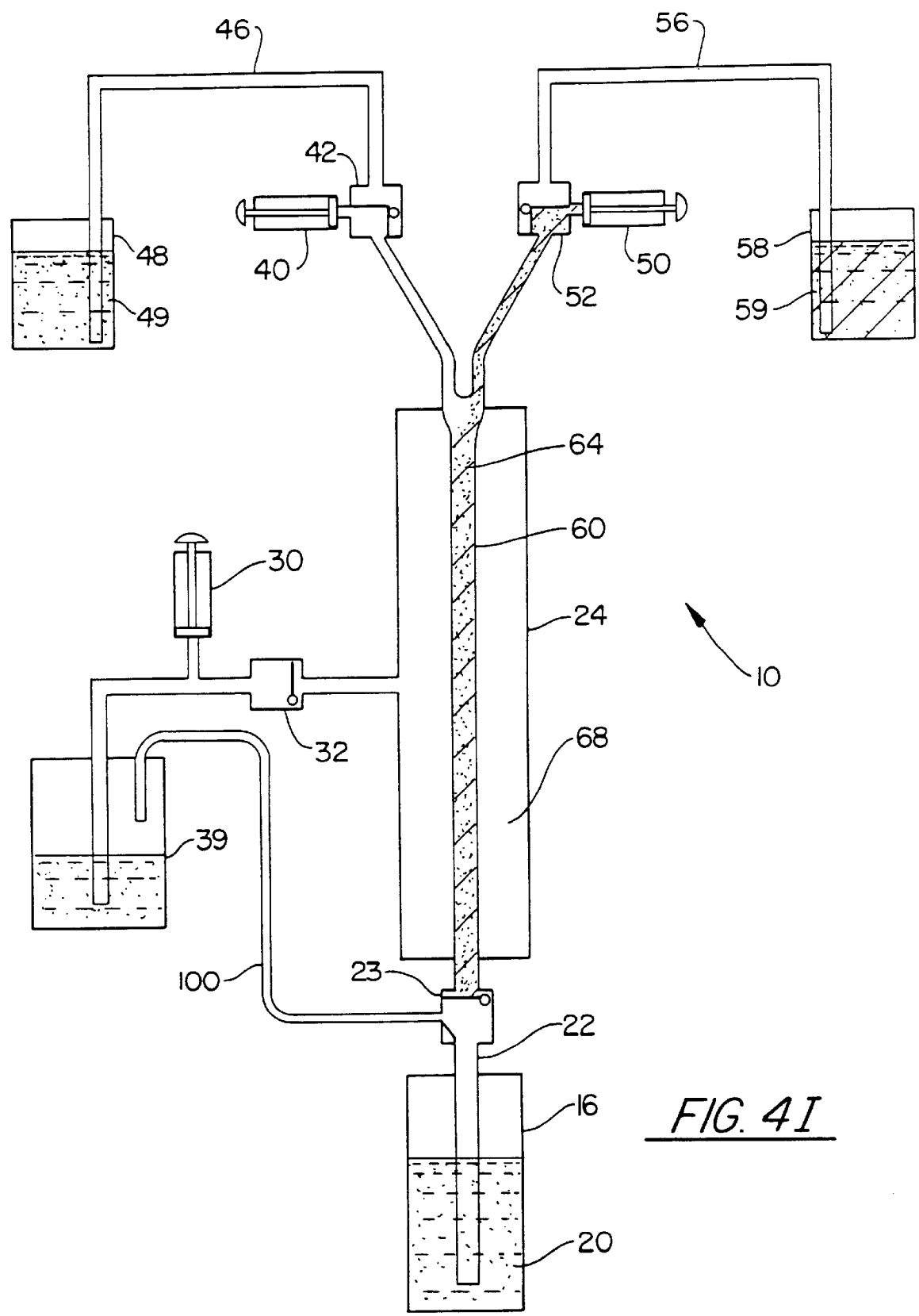
Figure 4J:
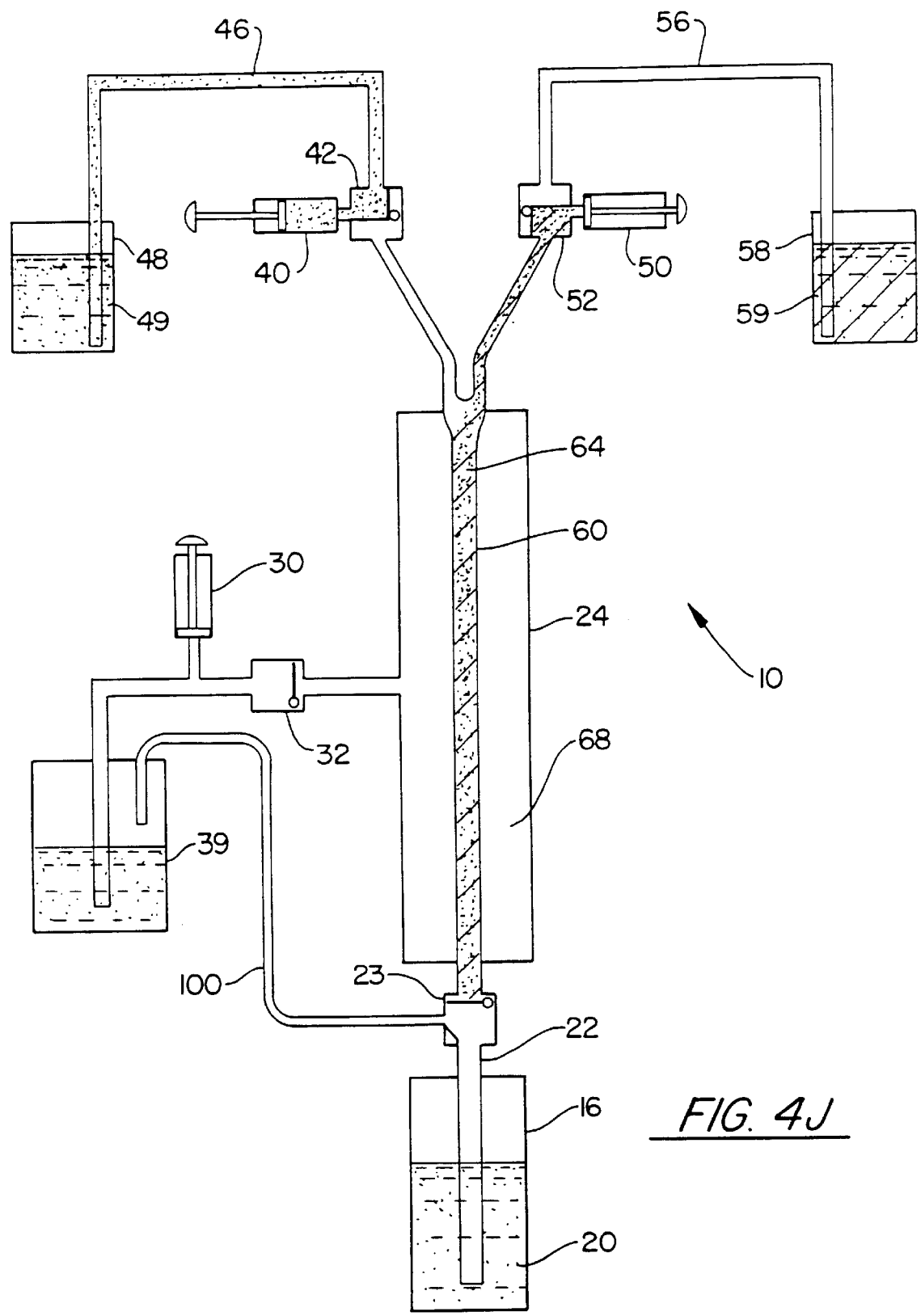

The apparatus 10 can be washed as shown in FIGS. 4H–K. The washing of the apparatus can be after each sample, after a predetermined number of samples, or upon fouling of the membrane 60. In the washing step, apparatus 10 is set up so that valve 23 is partially open, and valves 32 and 42 are closed. As shown in FIG. 4H, detergent solution valve 52 is then switched to the fill position and detergent solution pump 50 is activated to aspirate a predetermined volume of detergent solution 59, for example 3 ml, from detergent solution reservoir 58. As indicated in FIG. 4I, valve 52 is then switched to the dispense position and pump 50 is activated to dispense the aspirated volume of solution 59 through filtration device 24. Because valve 23 is partially open, solution 59 can flow through hose 100 into waste reservoir 39. To purge any detergent solution 59 remaining in device 24, as shown in FIG. 4J, buffer valve 42 is then switched to the fill position and buffer pump 40 is activated to aspirate a predetermined volume of buffer 49, for example 3 ml, from buffer reservoir 48.

Figure 4K:
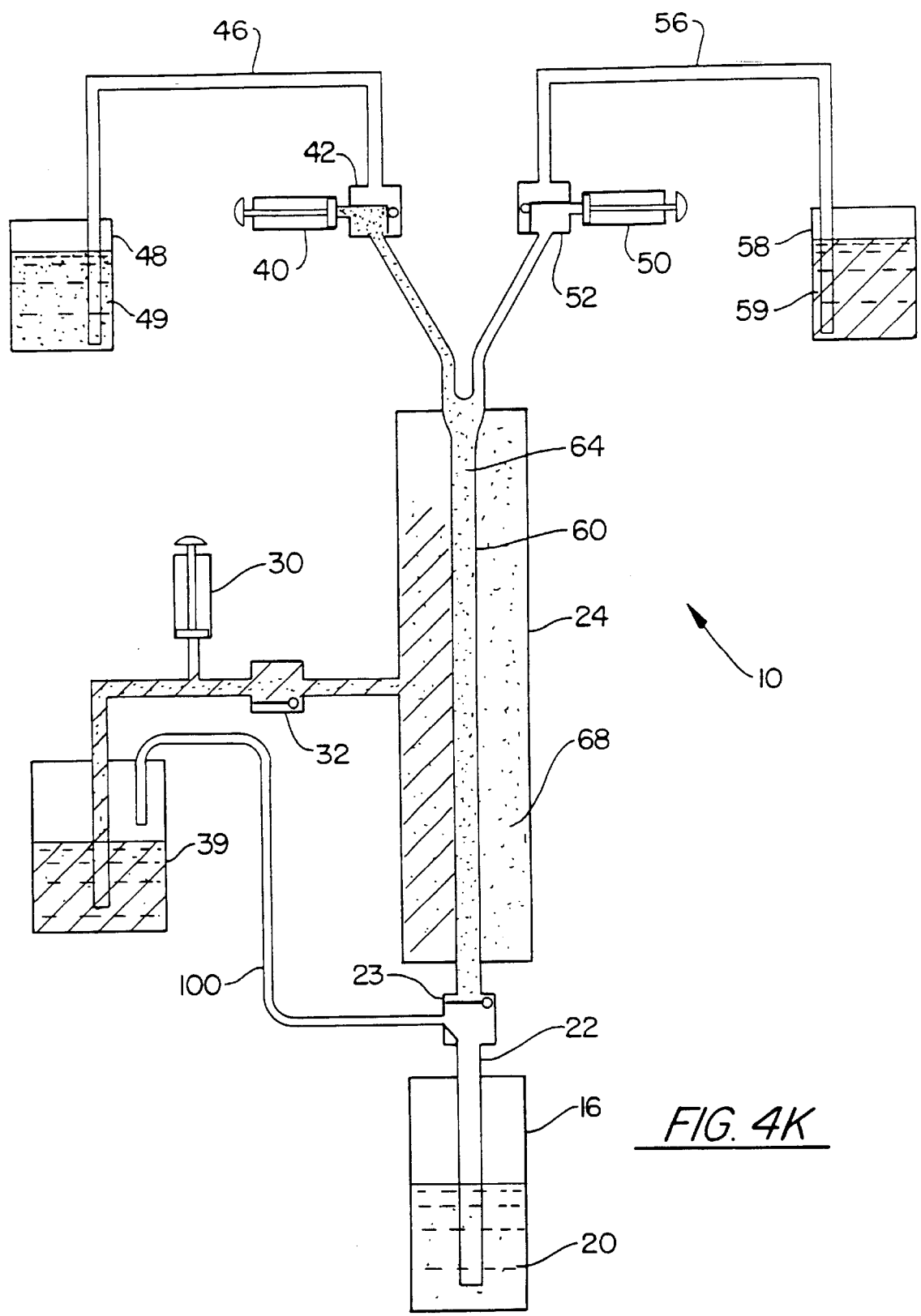

In FIG. 4K, prior to the buffer dispensing step, valve 23 can be closed and valve 32 can be switched to the open position. Valve 42 is switched to the dispense position and pump 40 is activated so that buffer 49 is dispensed and the remaining detergent solution 59 in the filtration device and buffer 49 are transferred to waste reservoir 39 by a waste hose. Alternatively, or in addition, valve 23 is switched to being partially open, and valve 32 is closed, and valve 42 is switched to the dispense position and pump 40 is activated to dispense the aspirated volume of buffer 49 through filtration device 24 and hose 100 into reservoir 39. The foregoing steps can be repeated so that device 24 is washed with multiple volumes of buffer prior to analysis of the next sample.

In a proposed commercial embodiment of the apparatus, valve 23 is eliminated from the apparatus. Moreover, in the proposed commercial embodiment, the Sample hose 22 comprises an aspiration probe that is known to those skilled in the art and is repositioned from the sample container 16 to a waste container (not shown) when detergent solution 59 or buffer 49 are dispensed through filtration device 24 to wash the filtration device 24 or sample hose 22 from previous sample mixtures. In one feature of this embodiment, the waste container comprises a cup that receives the waste. More specifically, the detergent solution or the buffer solution does not flow directly through either hose 100 into the sample container 16 or through valve 32. The sample hose 22 is repositioned from the sample container 16 to a waste container so that the detergent solution 59 or buffer 49 are dispensed into the waste container (not shown). Thereafter the waste is aspirated from the waste container to a larger waste reservoir. In the proposed commercial embodiment, the exterior of the aspiration probe is washed by prior art means of probe wiping.

Similarly, when diluting the sample mixture in the sample container 16, the buffer 49 does not flow directly from buffer reservoir 48 through hose 100. The buffer 49 does not flows from the buffer reservoir 48 through the sample hose 22 (aspiration probe) but instead flows through a separate tube (not shown) which is positioned next to the aspiration probe to pass buffer from the buffer reservoir 48 directly into the sample container 16. This feature enables rapid dilution of the sample mixture and enables the use of clean buffer to pass through the filter.

The method of using this proposed commercial embodiment is essentially the same as previous embodiments. More particularly, an automated method is provided for removing interferants from a mixture of a composition of interest and interferants by applying a vacuum force to a mixture of a composition of interest and interferants in a first sample container to cause the mixture to contact a filter; and then applying a force to the mixture in contact with the filter, whereby interferants in the mixture pass through the filter while the composition of interest in the mixture does not pass through the filter; and recovering the composition of interest from the filter.

As noted, a vacuum force rather than a positive pressure force is the preferred force used for removing the mixture from sample holder 16. In addition, the vacuum force also causes the interferants in the mixture to pass through the filter while the composition of interest is retained in the lumens 66. In the present preferred embodiment, the vacuum source is required to cause the interferants to pass through the lumens 66 because valve 23 has been eliminated. Also as previously noted, the utility of a vacuum force tends to preclude the aggregation of the particles of interest and clogging of the pores of the lumen 66.

In the proposed commercial embodiment, the buffer 49 is further used to recover the particles of interest from the lumens 66. The buffer is not used under positive pressure from pump 40 to force the interferants through the lumens 66.

Figure 5:
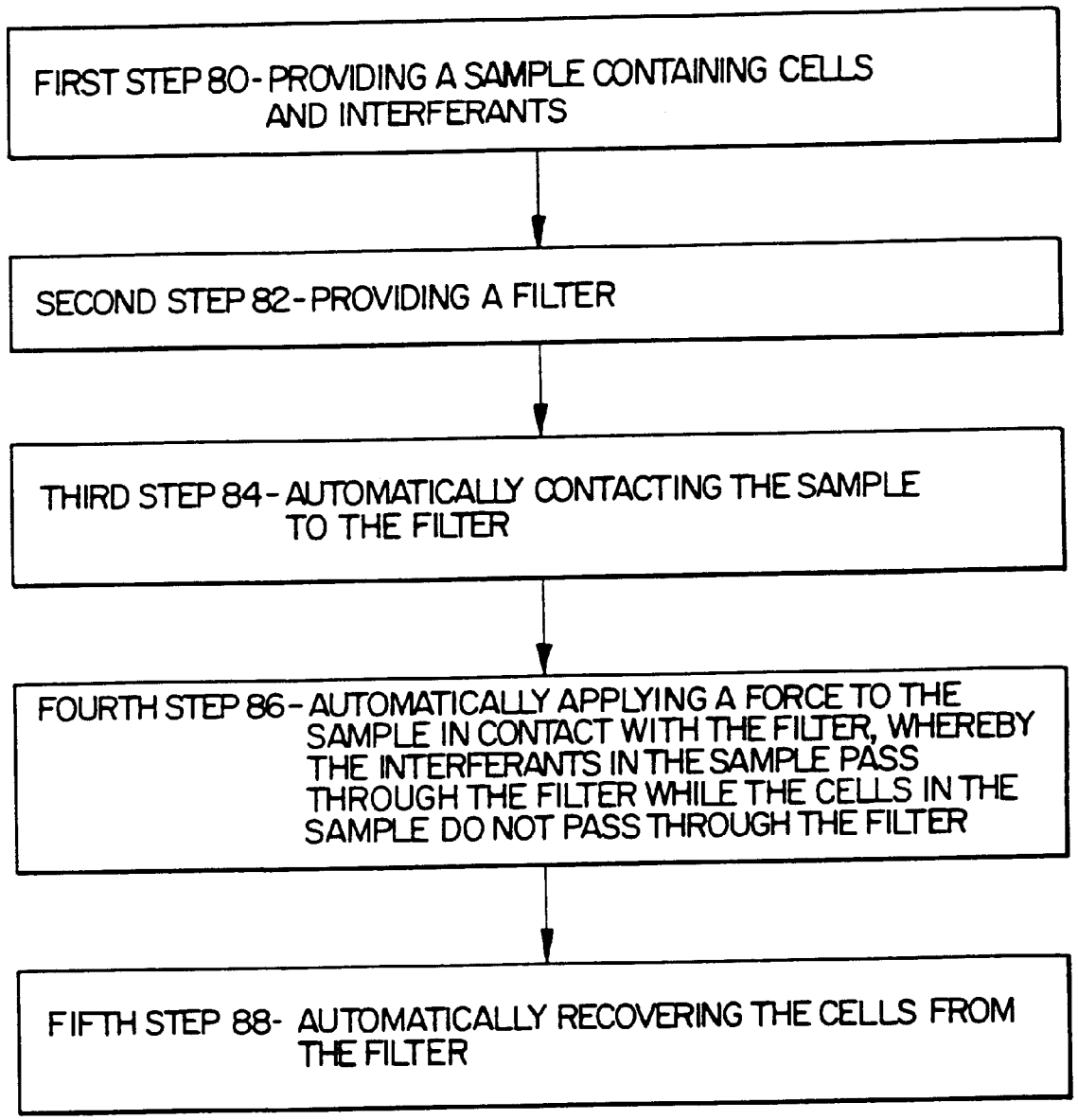
FIG. 5 is an outline of a method of the invention.

Referring now to FIG. 5, the invention also includes methods for removing interferants from a sample of cells. A preferred method for removing interferants from a sample of cells comprises a first step 80 of applying a vacuum force to a blood cell sample to cause the blood cell sample to leave the sample container 16 and contact a filter. As previously explained, this is accomplished by a vacuum force, which typically is capable of causing approximately 4 ml of a blood cell sample to be withdrawn from the sample container and pass through the membrane filter in approximately 7 seconds. As appreciated by one skilled in the art, the amount of blood cell sample withdrawn from the sample container 16 can be increased or reduced and the time can also be increase or reduced. The limitation on the vacuum force is that it will be less than the amount of force that would cause the cells to aggregate when being retained in the lumen 66. Preferably, the force will be less than that which would cause the cells to deform.

The method includes a second step 82 of applying a force to the blood cell sample in contact with the filter, whereby interferants in the blood cell sample pass through the filter while the cells of interest in the blood cell sample do not pass through the filter. In a preferred embodiment of the invention, the force that is applied to the blood cell sample to cause the interferants to pass through the filter is the same vacuum force which is used to withdraw the blood cell sample from the sample holder. However, it is appreciated that the force could be a separate hydraulic force which after the blood cell sample is withdrawn from the sample container 16, could be applied to the blood cell sample to push the blood cell sample into the lumen and through the membrane. However, it has been found that a vacuum is less damaging to cells. The limitation on the force is that it will be less than the amount of force, which would cause the cells to aggregate when being retained in the lumen 66. Preferably, the force will be less than that which would cause the cells to deform.

The method includes a third step 84 of recovering the cells from the filter. In a preferred embodiment, the cells are recovered by the apparatus of the invention wherein a volume of buffer is pumped through the top portion of the lumen causing the cells that were retained in the lumen to pass through the bottom portion of the lumen back into the sample container. Alternative, the retained blood cells can pass through the bottom portion of the lumen into a new sample container which can be employed to store the recovered blood cells.

In a more preferred embodiment of the present method, the blood cell sample is first diluted with at least one volume of buffer to each volume of blood cell sample. Even more preferable is that the blood cell sample be diluted with at least two volumes of buffer before entering the lumen to remove the interferants. It has been found that with a one volume dilution of the blood cell sample that greater than 70% of the interferants are removed from the blood cell sample, and with a two volume dilution, greater than 80% of the interferants are removed from the blood cell sample. A three volume dilution of the blood cell sample is preferred to remove greater than 90% of the interferants from the blood cell sample.

In a proposed commercial embodiment of the present method, the method can be run in several different protocols, P1, P2, P3 and P4. As recognized by those skilled in the art, alternative protocols of the method can be developed which can provide a greater percentage of elimination of interferants.

In P1, the blood cell sample is first diluted with at least one volume of buffer, preferably up to 4 volumes of buffer, to each volume of blood cell sample to form a diluted blood cell sample. Second, a vacuum force is applied to the diluted blood cell sample to aspirate the diluted blood cell sample from the sample container 16 and to cause the diluted blood cell sample to contact a filter. Third, a vacuum force is applied to the diluted blood cell sample in contact with the filter, whereby interferants in the diluted blood cell sample pass through the filter while the cells of interest in the diluted blood cell sample do not pass through the filter. Preferably, the vacuum force that is applied to the diluted blood cell sample to cause the interferants to pass through the filter is the same vacuum force that is used to withdraw the diluted blood cell sample from the sample holder. Fourth, the cells of interest are recovered into the sample container 16 by passing at least one volume of buffer, up to approximately 4 volumes of buffer, for each volume of blood cell sample through the lumen causing the cells of interest that were retained in the lumen to pass through the bottom portion of the lumen back into the sample container.

The steps of P2 comprise having the blood cell sample is first diluted with at least one volume of buffer, preferably up to 4 volumes of buffer, to each volume of blood cell sample to form a diluted blood cell sample. Second, a vacuum force is applied to the diluted blood cell sample to aspirate the diluted blood cell sample from the sample container 16 and to cause the diluted blood cell sample to contact a filter. Third, a vacuum force is applied to the diluted blood cell sample in contact with the filter, whereby interferants in the diluted blood cell sample pass through the filter while the cells of interest in the diluted blood cell sample do not pass through the filter. Preferably, the vacuum force that is applied to the diluted blood cell sample to cause the interferants to pass through the filter is the same vacuum force that is used to withdraw the diluted blood cell sample from the sample holder. Fourth, the cells of interest are recovered into the sample container 16 by passing at least one volume of buffer, up to approximately 4 volumes of buffer, for each volume of blood cell sample through the lumen causing the cells of interest that were retained in the lumen to pass through the bottom portion of the lumen back into the sample container. Fifth, a vacuum force is applied to the recovered cells of interest to aspirate the recovered cells of interest from the sample container 16 and to cause the cells of interest and the recovery buffer to contact the filter. Sixth, a vacuum force is applied to the cells of interest and recovery buffer which is in contact with the filter, whereby any further remaining interferants in the lumen 66 pass through the filter while the cells of interest do not pass through the filter. Similar to before, the vacuum force that is applied to the buffer to cause the any further remaining interferants to pass through the filter is the same vacuum force that is used to withdraw the cells of interest and recovery buffer from the sample holder. Seventh, the cells of interest are again recovered into the sample container 16 by passing approximately one volume of buffer, for each volume of blood cell sample, through the lumen causing the cells of interest that were retained in the lumen to pass through the bottom portion of the lumen back into the sample container.

In P3, the blood cell sample is first diluted with at least one volume of buffer, preferably up to 4 volumes of buffer, to each volume of blood cell sample to form a diluted blood cell sample. Second, a vacuum force is applied to the diluted blood cell sample to aspirate the diluted blood cell sample from the sample container 16 and to cause the diluted blood cell sample to contact a filter. Third, a vacuum force is applied to the diluted blood cell sample in contact with the filter, whereby interferants in the diluted blood cell sample pass through the filter while the cells of interest in the diluted blood cell sample do not pass through the filter. Preferably, the vacuum force that is applied to the diluted blood cell sample to cause the interferants to pass through the filter is the same vacuum force that is used to withdraw the diluted blood cell sample from the sample holder. Fourth, the sample container 16 is filled with approximately up to 5 volumes of buffer to each volume of blood cell sample. Fifth, a vacuum force is applied to the buffer to aspirate the buffer from the sample container 16 and to cause the buffer to contact the cells of interest and the filter. Sixth, a vacuum force is applied to the buffer which is in contact with the filter, whereby any remaining interferants in the lumen 66 pass through the filter while the cells of interest do not pass through the filter. Similar to before, the vacuum force that is applied to the buffer to cause the interferants to pass through the filter is the same vacuum force that is used to withdraw the buffer from the sample holder. Seventh, the cells of interest are recovered into the sample container 16 by passing at least one volume of buffer, up to approximately 4 volumes of buffer, for each volume of blood cell sample through the lumen causing the cells of interest that were retained in the lumen to pass through the bottom portion of the lumen back into the sample container. Eighth, a vacuum force is applied to the recovered cells of interest to aspirate the recovered cells of interest from the sample container 16 and to cause the cells of interest and the recovery buffer to contact the filter. Ninth, a vacuum force is applied to the cells of interest and recovery buffer which is in contact with the filter, whereby any further remaining interferants in the lumen 66 pass through the filter while the cells of interest do not pass through the filter. Similar to before, the vacuum force that is applied to the buffer to cause the any further remaining interferants to pass through the filter is the same vacuum force that is used to withdraw the cells of interest and recovery buffer from the sample holder. Tenth, the cells of interest are again recovered into the sample container 16 by passing approximately one volume of buffer, for each volume of blood cell sample, through the lumen causing the cells of interest that were retained in the lumen to pass through the bottom portion of the lumen back into the sample container.

The steps of P4 comprise the blood cell sample is first diluted with at least one volume of buffer, preferably up to 4 volumes of buffer, to each volume of blood cell sample to form a diluted blood cell sample. Second, a vacuum force is applied to the diluted blood cell sample to aspirate the diluted blood cell sample from the sample container 16 and to cause the diluted blood cell sample to contact a filter. Third, a vacuum force is applied to the diluted blood cell sample in contact with the filter, whereby interferants in the diluted blood cell sample pass through the filter while the cells of interest in the diluted blood cell sample do not pass through the filter. Preferably, the vacuum force that is applied to the diluted blood cell sample to cause the interferants to pass through the filter is the same vacuum force that is used to withdraw the diluted blood cell sample from the sample holder. Fourth, the sample container 16 is filled with approximately up to 5 volumes of buffer to each volume of blood cell sample. Fifth, a vacuum force is applied to the buffer to aspirate the buffer from the sample container 16 and to cause the buffer to contact the cells of interest and the filter. Sixth, a vacuum force is applied to the buffer which is in contact with the filter, whereby any remaining interferants in the lumen 66 pass through the filter while the cells of interest do not pass through the filter. Similar to before, the vacuum force that is applied to the buffer to cause the interferants to pass through the filter is the same vacuum force that is used to withdraw the buffer from the sample holder. Seventh, the cells of interest are recovered into the sample container 16 by passing at least one volume of buffer, up to approximately 4 volumes of buffer, for each volume of blood cell sample through the lumen causing the cells of interest that were retained in the lumen to pass through the bottom portion of the lumen back into the sample container. Eighth, a vacuum force is applied to the diluted blood cell sample to aspirate the diluted blood cell sample from the sample container 16 and to cause the diluted blood cell sample to contact a filter. Ninth, a vacuum force is applied to the diluted blood cell sample in contact with the filter, whereby interferants in the diluted blood cell sample pass through the filter while the cells of interest in the diluted blood cell sample do not pass through the filter. Preferably, the vacuum force that is applied to the diluted blood cell sample to cause the interferants to pass through the filter is the same vacuum force that is used to withdraw the diluted blood cell sample from the sample holder. Tenth, the sample container 16 is filled with approximately up to 5 volumes of buffer to each volume of blood cell sample. Eleventh, a vacuum force is applied to the buffer to aspirate the buffer from the sample container 16 and to cause the buffer to contact the cells of interest and the filter. Twelfth, a vacuum force is applied to the buffer which is in contact with the filter, whereby any remaining interferants in the lumen 66 pass through the filter while the cells of interest do not pass through the filter. Similar to before, the vacuum force that is applied to the buffer to cause the interferants to pass through the filter is the same vacuum force that is used to withdraw the buffer from the sample holder. Thirteenth, the cells of interest are recovered into the sample container 16 by passing at least one volume of buffer, up to approximately 4 volumes of buffer, for each volume of blood cell sample through the lumen causing the cells of interest that were retained in the lumen to pass through the bottom portion of the lumen back into the sample container. Fourteenth, a vacuum force is applied to the recovered cells of interest to aspirate the recovered cells of interest from the sample container 16 and to cause the cells of interest and the recovery buffer to contact the filter. Fifteenth, a vacuum force is applied to the cells of interest and recovery buffer which is in contact with the filter, whereby any further remaining interferants in the lumen 66 pass through the filter while the cells of interest do not pass through the filter. Similar to before, the vacuum force that is applied to the buffer to cause the any further remaining interferants to pass through the filter is the same vacuum force that is used to withdraw the cells of interest and recovery buffer from the sample holder. Sixteenth, the cells of interest are again recovered into the sample container 16 by passing approximately one volume of buffer, for each volume of blood cell sample, through the lumen causing the cells of interest that were retained in the lumen to pass through the bottom portion of the lumen back into the sample container. Seventeenth, a vacuum force is applied to the recovered cells of interest to aspirate the recovered cells of interest from the sample container 16 and to cause the cells of interest and the recovery buffer to contact the filter. Eighteenth, a vacuum force is applied to the cells of interest and recovery buffer which is in contact with the filter, whereby any further remaining interferants in the lumen 66 pass through the filter while the cells of interest do not pass through the filter. Similar to before, the vacuum force that is applied to the buffer to cause the any further remaining interferants to pass through the filter is the same vacuum force that is used to withdraw the cells of interest and recovery buffer from the sample holder. Nineteenth, the cells of interest are again recovered into the sample container 16 by passing approximately one volume of buffer, for each volume of blood cell sample, through the lumen causing the cells of interest that were retained in the lumen to pass through the bottom portion of the lumen back into the sample container.

The steps of this method can be accomplished using the apparatus of the invention which will provide automation of the steps described above. As defined herein, one cycle of the method is considered to be one wash cycle of the blood cell sample. More specifically, one wash cycle of the blood cell sample comprises applying a vacuum force to a blood cell sample to cause the blood cell sample contact a filter; applying a force to the blood cell sample in contact with the filter, whereby interferants in the blood cell sample pass through the filter while the cells in the blood cell sample do not pass through the filter; and recoverying the cells from the lumen. Accordingly, one wash cycle of the blood cell sample wash cycle of this invention can be performed in less than 5 minutes. Preferably, one wash cycle of the blood cell sample is performed in less than 3 minutes, and more preferably less than 1 minute. In an even more preferred embodiment one wash cycle of the blood cell sample is performed in less than 30 seconds. Finally, in a most preferred embodiment, one wash cycle of the blood cell sample is performed in less than 15 seconds.

It has been found that multiple wash cycles cause the cells to deteriorate such as shrinkage of the cell membranes and rupture of the cell membranes. It has been further found that the addition of a serum substance to the buffer which dilutes the blood cell sample minimizes the deterioration. As defined herein, serum substance comprises cholesterol, cholesterol esters, and cholesterol which has been combined with one or more other compounds found in serum plasma, and mixtures thereof. Preferably, such other compounds further comprise lipoproteins and phospholipids, and mixtures thereof. As appreciated by those skilled in the art, typically cholesterol will contain approximately 30% esters. As further appreciated by those skilled in the art, the lipoprotein will maintain the cholesterol in an aqueous solution. Preferably, the serum substance is selected from the group comprising cholesterol, cholesterol esters, lipoprotein cholesterol, lipoprotein cholesterol esters, cholesterol combined with phospholipids and mixtures thereof.

FIG. 14 depicts an increase in the recovery of cellular events as related to the percent addition of fetal calf serum in a buffer. In this figure, the blood cell sample was washed 3 times with a hollow fiber membrane apparatus shown as "Invention" in the figure. An increase of fetal calf serum indicates that there will be an increase in the percent of cells recovered after multiple wash cycles.

It has also been found that one wash cycle of the blood cell sample without the addition of a serum substance eliminates the banana appearance between the lymphocytes and neutrophils subpopulations in histograms of blood cell samples containing a high lipid content.

In an example of the present method, first step 80 is performed by providing a sample of cells such as a 100 microliters of whole human blood obtained by venipuncture from a human subject. If the removal of erythrocytes is desired, the sample can be diluted in a reagent which lyses red blood cells such as 600 microliters of formic acid, and then further diluted by addition of a reagent that neutralizes the red blood cell lysing agent such as 265 microliters of a carbonate buffer. Optionally, a fixative such as 100 $\mu$l of a paraformaldehyde solution can also be added to fix the cell sample. The blood cell sample is diluted to a total volume of about 4 ml with an isotonic buffer. Suitable reagents for these steps can be obtained from Beckman Coulter, Inc. (IMMUNOPREP™ reagent system part no. 7546999 or SCATTER PAK™ reagent system). A vacuum force is then applied to the diluted blood cell sample to cause it to contact a filter. Preferably the filter is a hollow fiber membrane (e.g., Cat# CFP-6-D-H22LA from A/G Technology Corporation).

In second step 82, a force is applied to the blood cells sample which is in contact with the filter to cause the interferants in the diluted blood cell sample to pass through the filter while the cells of interest in the blood cells sample are retained by the filter. More specifically, the cells of interest in the diluted blood cell sample do not pass through the filter. When the hollow fiber membrane is used, the cells of interest will be retained in the lumen. Preferably, a vacuum force is applied to the blood cell sample to cause the interferants to pass through the lumen while the cells of interest are retained in the lumen.

In a most preferred embodiment, the vacuum force that is used to cause the interferants to pass through the filter also aspirates the blood cell sample from the sample container. More specifically, the filtration device is in fluid communication with the sample container since it is filled with a buffer. Therefore, when a sufficient vacuum force is applied to the diluted blood cell sample in the sample container, the diluted blood cell sample is aspirated from the sample container into the filtration device and the interferants pass through the filter. This is accomplished by a continuous flow of the blood cell sample from the sample container through the filter. As previously discussed, the apparatus of this invention can automatically apply the vacuum force necessary to perform these functions.

The Third step 84 is recovering the cells from the filter. This can be accomplished by providing a force, such as a flow of liquid, to the filter in a direction opposite the direction from which the blood cell sample contacted the filter in step 80. The flow of liquid will move the cells of interest away from the filter. The recovered cells can thereafter be transported by fluid communication to an analytical instrument. Preferably, the recovered cells are returned to a test tube that is then transported to an instrument for analysis.

Figure 6:
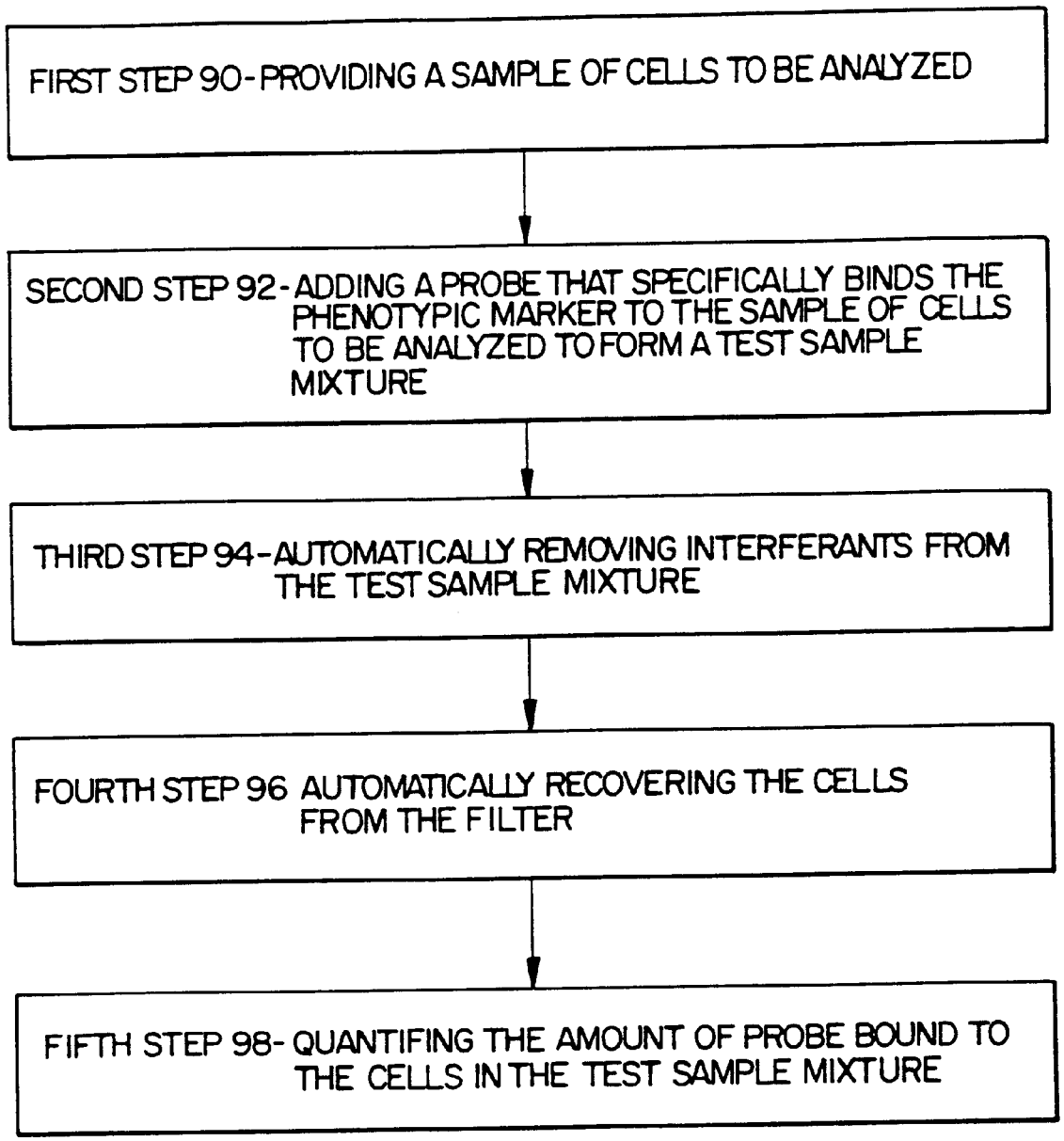
FIG. 6 is an outline of another method of the invention.

Referring now to FIG. 6, methods for analyzing cells for phenotypic markers are also included in the invention. A preferred method of analyzing a phenotypic marker on cells within a sample includes: a first step 90 of adding a probe that binds the phenotypic market to the sample of cells to be analyzed to form a test sample mixture; a second step 92 of applying a vacuum force to a blood cell sample to cause the blood cell sample contact a filter; a third step 94 of applying a force to the blood cell sample in contact with the filter, whereby interferants in the blood cell sample pass through the filter while the cells in the blood cell sample do not pass through the filter; a fourth step 96 of recovering the cells from the filter. The method can further include a fifth step 98 (not shown) of quantifying the amount of probe and differentiating the cell populations.

Steps 92, 94 and 96 can be performed as described above for FIG. 5 for Steps 80, 82 and 84 respectively. Step 98 can be performed by analyzing the test sample from which the interferants have been removed using flow cytometry or a similar analytical device.

For example, in a preferred version of this method, first step 90, a saturating concentration of a fluorescently-labeled antigen-specific antibody is added to the blood cell sample to form the test sample mixture. And fifth step 98 can be performed by running the processed test sample mixture on a flow cytometer equipped to quantitatively measure the amount of fluorescently-labeled antigen-specific antibody associated with each cell in the processed test sample mixture.

The method of the present invention has broad utility to remove interferants from a mixture of a composition of interest and interferants by applying a vacuum force to a first container containing a mixture of a composition of interest and interferants to cause the mixture containing the composition of interest and interferants to contact a filter; applying a force to said mixture in contact with the filter, whereby interferants in the mixture pass through the filter while the complex of interest does not pass through the filter; and recovering the complex of interest from the filter. Alternatively, the method of the present invention includes removal interferants from a mixture of a composition of interest and interferants by applying a vacuum force to a first container containing a mixture of a composition of interest and interferants to cause the mixture containing the composition of interest and interferants to contact a filter; applying a force to said mixture in contact with the filter, whereby composition of interest in the mixture pass through the filter while the interferant does not pass through the filter; and recovering the composition of interest. An example of the utility of this alternative method comprises the separation of serum from whole blood, wherein the composition of interest, serum, would pass through the filter, and interferants, cells and other biological substances and particles, would be retained in the filter. The serum would be recovered for analysis or for any other desired purpose.

The apparatus and method of the present invention has several advantages. First, the apparatus and method of the present invention can utilize small quantities of the mixture of the composition of interest and interferants. This is advantageous in that the prior art apparatus and methods that typically require batch quantities of at least 50 milliliters of a mixture to be transferred through a pump to contact a filter. In the instant apparatus and method, less than 50 milliliters, preferably less than 10 milliliters and more preferably less than 5 and most preferably less than 1 milliliter is used. Another advantage of the present apparatus and method of the present invention is that a cycle of the method can be automatically accomplished and within a shorter period of time than conventional separation techniques known in the art, such as centrifugation, use of magnetic beads, electrophoresis, and known filtration methods.

From the foregoing, it can be appreciated that the apparatus and methods of the invention facilitate the removal of interferants from a mixture of a composition of interest and interferants wherein the composition of interest is to be analyzed. The invention will be further described in the following examples, which do not limit the scope of the claims.

EXAMPLE 1

Apparatus

An apparatus was built with a hollow fiber membrane cartridge cat# CFP-6-D-H221A from A/G Technology Corporation. The apparatus included a carousel-type cell sample holder adapted to hold several 12×75 mm culture tubes. Alternatively, the apparatus can include other types of tube holders such as a cassette. The apparatus also included various hoses, valves, and pumps so that a mixture of a composition of interest and interferants can be aspirated from the tube, filtered through the hollow fiber membrane cartridge to remove interferants from the mixture, and then returned to the tube. As described in the detailed description, the apparatus also included various hoses, valves, and pumps so that waste fluids (for example, filtrate containing interferants) could be removed to a waste reservoir, and the hollow fiber membrane could be cleaned for use with additional mixtures. The apparatus also included a computerized system for coordinating the mixture washing process and the membrane cleaning procedure. A carousel-type mixture holder was rotatable and also controlled by the computerized system such that after processing a first mixture, a second tube containing a second mixture could be repositioned to allow the mixture to be aspirated from the tube, filtered through the hollow fiber membrane cartridge to remove interferants from the mixture, and then returned to the second tube. This cycle was repeatable such that all mixtures in the carousel could be washed.

EXAMPLE 2

Method of Washing Cells

Various methods, including a method employing the apparatus of Example 1, were used for removing interferants from a cell sample processed according to the general method described below. A cell population was stained with a fluorescently labeled antibody according to standard techniques. For example, 100 ul of whole human blood was obtained by venipuncture from a human subject, and then 10 ul of a 1 mg/ml solution of an antigen-specific FITC-labeled antibody was added to the blood sample. Samples were then incubated for 10 minutes at room temperature, after which erythrocytes were lysed using Beckman Coulter's IMMUNOPREP research system and TQ-Prep apparatus according to the manufacturer's instructions (600 µl of solution A for 8 seconds with mixing; 265 µl of solution B for 10 seconds with mixing; and 100 µl of solution C for 10 seconds with mixing). Separate aliquots of the processed blood cells samples were then subjected to one of three different protocols:

A. diluted with an isotonic buffer to a total volume of about 4 ml and then washed 1 time per a "Quick Spin" wash protocol. The Quick Spin was protocol means centrifuge 400× g for 5 minutes using a standard centrifuge, decant supernatant, and resuspend in 1 ml of an isotonic buffer;

B. diluted with an isotonic buffer to a total volume of about 4 ml and then washed 1 time per a "Sorvall" protocol using a Sorvall® Cell Washer 2 (auto mode 80 seconds; high speed 2950–3000 rpm; decant 600 rpm) according to the manufacturer's instructions (washed cells resuspended in final volume of 1 ml isotonic buffer); or C. diluted with an isotonic buffer to a total volume of about 4 ml and then washed 1 time using the apparatus described in Example 1 (washed cells in final volume of 1 ml isotonic buffer).

EXAMPLE 3

Analysis of Cell Samples

Figure 7:
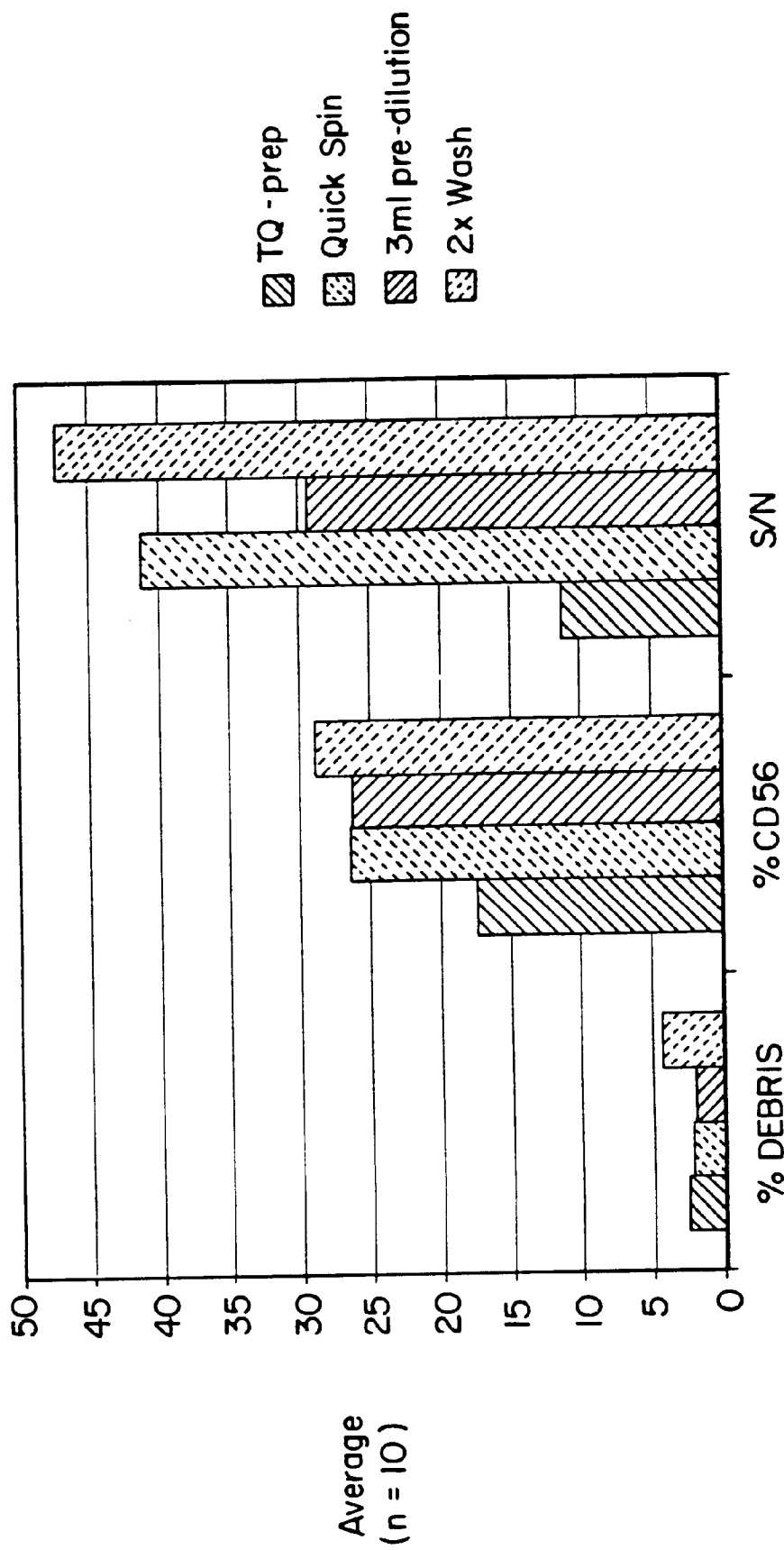
FIG. 7 is a graph showing data obtained from flow cytometric analysis of blood cell samples reacted with fluorescent labeled CD56 monoclonal antibodies. Data are presented as percent debris, percent CD56+, and signal-to-noise ratio. Data shown are averages of ten replicates using one donor.

Samples of whole human blood were reacted with a fluorescent labeled monoclonal antibody directed against the cell surface antigen designated CD56, erythrocyte lysed and fixed according to Example 2. "TQ-Prep" samples were not washed. "Quick Spin" samples were washed according to the Quick Spin protocol described in Example 2. "3 ml predilution" samples were washed one time using a hollow fiber membrane apparatus according to the protocol described in Example 2C. "2× wash" samples were washed two times (second wash with a 2 ml predilution) using a hollow fiber membrane apparatus according to the protocol described in Example 2C. The processed blood cell samples were then subjected to flow cytometric analysis using a COULTER EPICS XL flow cytometer according to the manufacturer's instructions. Results for % debris as determined by light scatter analysis, % CD56 positive cells, and signal-to-noise ratio (extrapolated from histograms) are shown in FIG. 7.

The amount of debris was low for all samples, although more debris was noted in the samples subjected to two washings with the hollow fiber membrane apparatus. The increase of debris was caused by cell degradation because no serum substance was employed in the diluent. The percent of CD56 cells was about the same whether the Quick Spin was used or the hollow fiber membrane apparatus was used. Signal-to-noise ratios were greatly improved over the no wash control, no matter which washing protocol was used. Washing the sample two times with the hollow fiber membrane apparatus produced the best signal-to noise ratio.

In similar experiments, for unwashed samples the average percent of debris was 10.3% and the average signal to noise ratio was 11.4. As defined herein, debris means events falling below threshold measurement values. In comparison, using the hollow fiber membrane apparatus, the average percent of debris was 2.5%, which means that greater than 75% of the original 10.3% of debris was removed. In addition, the average signal to noise ratio was 23.8, which means that there was greater than a 200% improvement in the signal to noise ratio. Using the Quick Spin protocol, the average percent debris was 2.6% and the average signal to noise ratio was 38.7. In other experiments, when cell samples were washed 2 or 3 times with the hollow fiber membrane apparatus more interferants were removed and the signal to noise ratio further improved.

EXAMPLE 4

Evaluation of Cell Recovery

Figure 8:
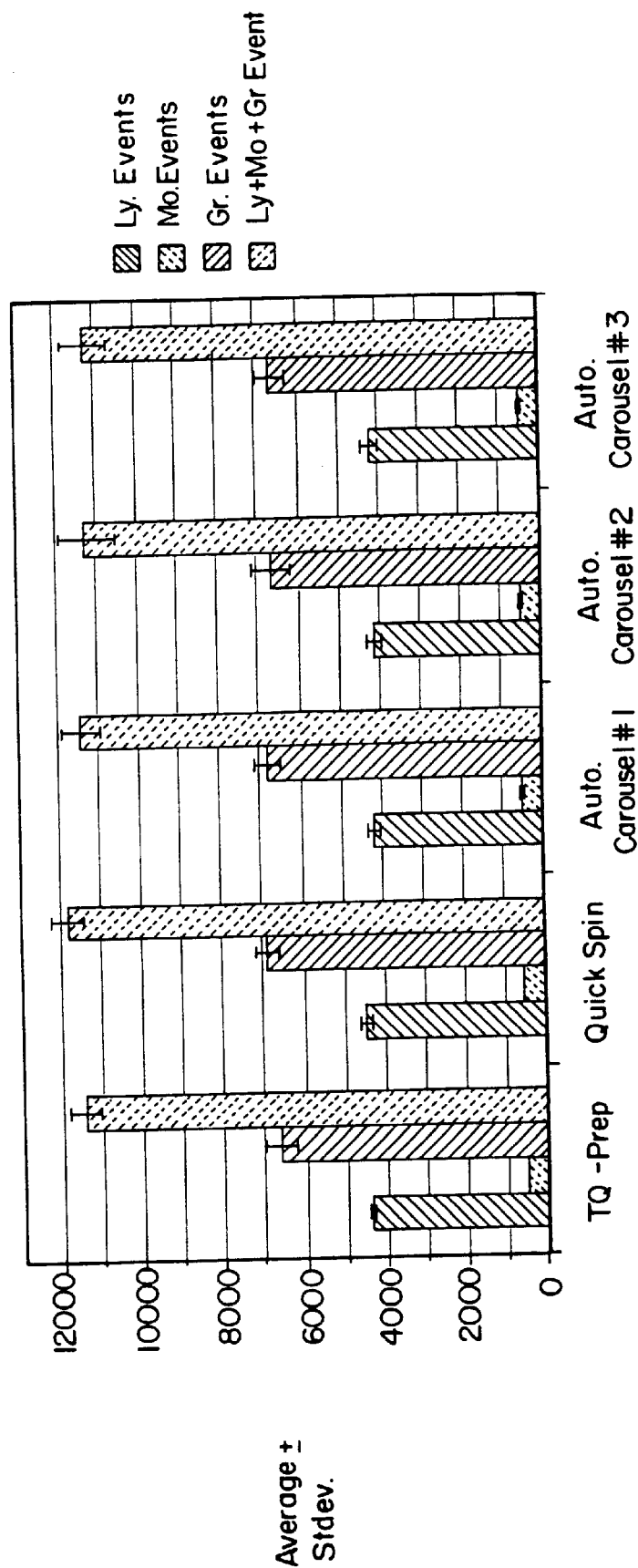
FIG. 8 is a graph showing data obtained from flow cytometric analysis of cell recovery from erythrocyte-lysed and fixed blood cell samples subject to different washing protocols. Data from lymphocyte ("Ly.") fractions, monocyte ("Mo.") fractions, granulocyte ("Gr.") fractions, and a combination of all three fractions are shown. Fractions were selected based on light scatter. Data are shown as averages with error bars indicating standard deviations.

Samples of whole human blood were processed, and washed according to the protocols described in Example 2, and then subjected to flow cytometric analysis using an EPICS XL flow cytometer according to the manufacturer's instructions. As shown in FIG. 8, results for cell recovery (number of indicated type of cells recovered from 100 microliter sample of whole blood after processing) show that little or no cell loss occurs in either the lymphocyte, monocyte, granulocyte (cell type determined by light scatter) fractions of the samples. Moreover, cell recovery using the apparatus of Example 1 was about equivalent to that obtained using the Quick Spin protocol. "TQ-Prep" samples (n=5) were not washed; "Quick Spin" samples (n=5) were washed according to the Quick Spin protocol described herein. "Auto" samples (n=32) were washed one time using a hollow fiber membrane apparatus.

EXAMPLE 5

Accuracy

Figure 9:
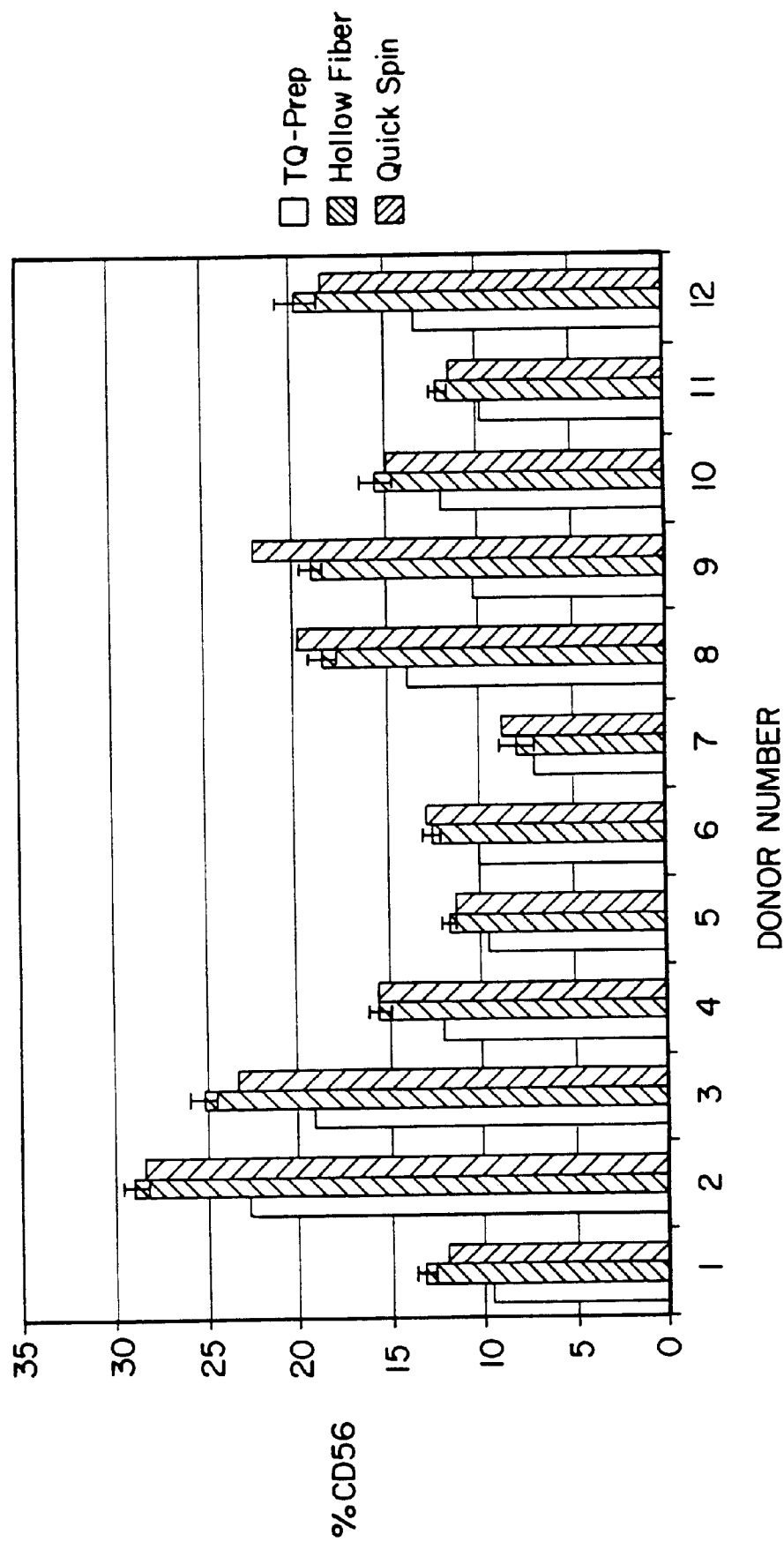
FIG. 9 is a graph showing data obtained from flow cytometric analysis of blood cell samples taken from 12 donors and stained for CD56, erythrocyte-lysed, and fixed. Data are presented as percent CD56+, and are shown as averages of two to twelve replicates per donor. Error bars indicate standard deviation.

Samples of whole human blood from several different donors were stained for CD56, processed, and washed according to the protocols described in Example 2. "TQ-Prep" samples were not washed; "Quick Spin" samples were washed according to the Quick Spin protocol described herein; and "Hollow Fiber" samples were washed one time using a hollow fiber membrane apparatus. The samples were then subjected to flow cytometric analysis using an EPICS XL flow cytometer according to the manufacturer's instructions. As shown in FIG. 9, the percentage of cells that were CD56$^+$ varied from donor to donor but, for any one donor, was about the same whether the Quick Spin was used or the hollow fiber membrane apparatus was used.

EXAMPLE 6

Precision

Thirty-two aliquots of one sample of whole human blood were stained for CD56, processed, and washed according to the protocols described in Example 2, and then subjected to flow cytometric analysis using a COULTER EPICS XL flow cytometer according to the manufacturer's instructions to determine the percent of CD56$^+$ cells in each aliquot. The average percent of CD56$^+$ cells among the aliquots was 17.44% with a standard deviation of 0.74 and a coefficient of variation of 4.27%. In a similar experiment using 28 aliquots, the average percent of CD56$^+$ cells among the aliquots was 15.6% with a standard deviation of 0.6 and a coefficient of variation of 3.5%.

EXAMPLE 7

Cell Carryover

Figure 10:
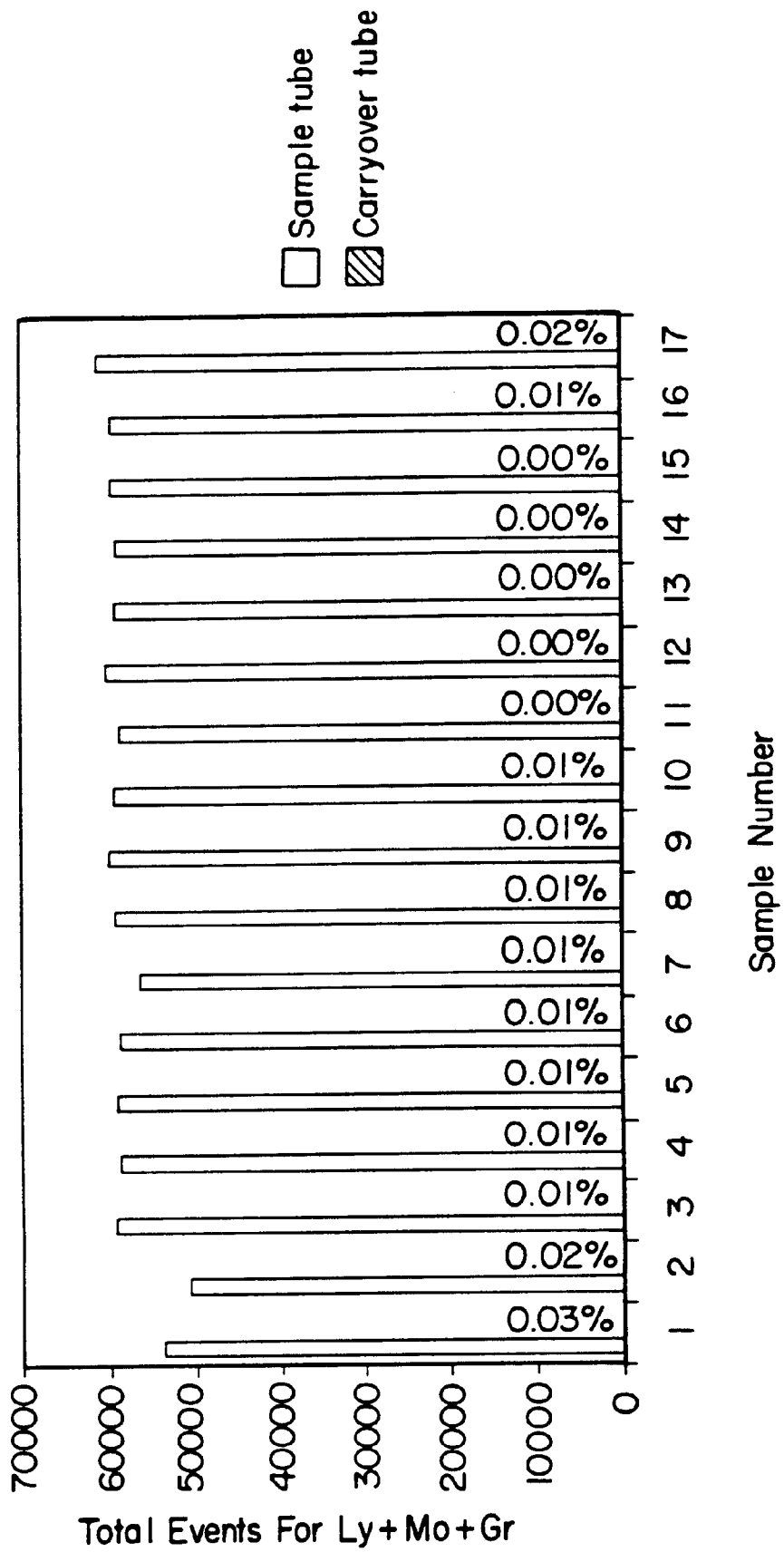
FIG. 10 is a graph showing the amount of cell carryover from concentrated cell samples washed with a hollow fiber membrane apparatus. After washing the cell sample and then cleaning the hollow fiber membrane, blank sample tubes were "washed" using the same hollow fiber membrane. The number of cells carried over from the cell sample to the blank sample tube were quantified using flow cytometry. Data are shown as percent of cells from cell sample carried over to blank sample. Seventeen samples from one donor were tested. The percent of carryover cells from the original total number of events is 0.03% or less. Consequently, FIG. 10 does not show a bar for the number of cells that were carry overed.

Whole blood cell samples were processed as described in Example 2 and then concentrated to four times normal cell concentrations. Each sample was then washed using the apparatus of Example 1 (per the protocol of Example 2C with cleaning of the hollow fiber membrane after sample washing). The apparatus was then used to "wash" a blank sample containing only buffer without cells. The blank sample was analyzed for the presence of cells using a flow cytometer. As shown in FIG. 10, carryover of cells from test to test was very low, ranging from 0.00% to 0.03% of cells being carried over to subsequent analysis.

EXAMPLE 8

Other Applications

The apparatus and methodology of the invention are also suitable for other applications such as protein analysis of urine. In addition, applications which have traditionally utilized centrifugation as part of their cellular analysis method are specifically envisioned for use with the disclosed hollow fiber membrane apparatus and method described herein. For example, many different cell populations have been analyzed using the apparatus. Additionally, many different probe types have been used in the invention. For instance, aside from erythrocyte-depleted whole blood samples, the hollow fiber membrane apparatus has been successfully used with cell lines, purified white blood cell subsets; erythrocytes; platelets; bone marrow cells; and cells in cerebrospinal, synovial, peritoneal, ascites, pleural, pericardial fluids and homogenized tissue. The erythrocyte agglutination techniques commonly practiced in the blood banking field for the typing of blood and for compatibility testing, which are traditionally centrifugation dependent, can be readily adapted for performance using the methodology and apparatus of the invention. Probes that have been successfully used in the invention include fluorescently labeled monoclonal antibodies that are specific for the cell surface antigens such as immunoglobulin, kappa and lambda factors, CD5, CD7, CD10, CD13, CD19, CD33, CD34, CD38, CD41, CD45, CD 41, CD42b, CD 61, CD63, CD64, CD71, and CD117; as well as intracellular antigens such as various types of hemoglobin. Various other antibody and non-antibody probes such as chemical and biologic constructs that bind to receptor molecules on the cell surface, enzymatic substrates which react with cellular enzymes within the cell, antibody and non-antibody probes which react with cytoplasmic antigens within the cell, DNA and RNA probes which react with nucleic acids sequences within the cells and various intracellular dyes that react with cytoplasmic and nuclear structures within the cell are expected to be compatible with the invention. It is thus envisioned that most types of cells and probes are compatible with the invention, especially if the selected cell type is larger and the selected probe is smaller than the pores of the selected hollow fiber membrane.

Figure 11:
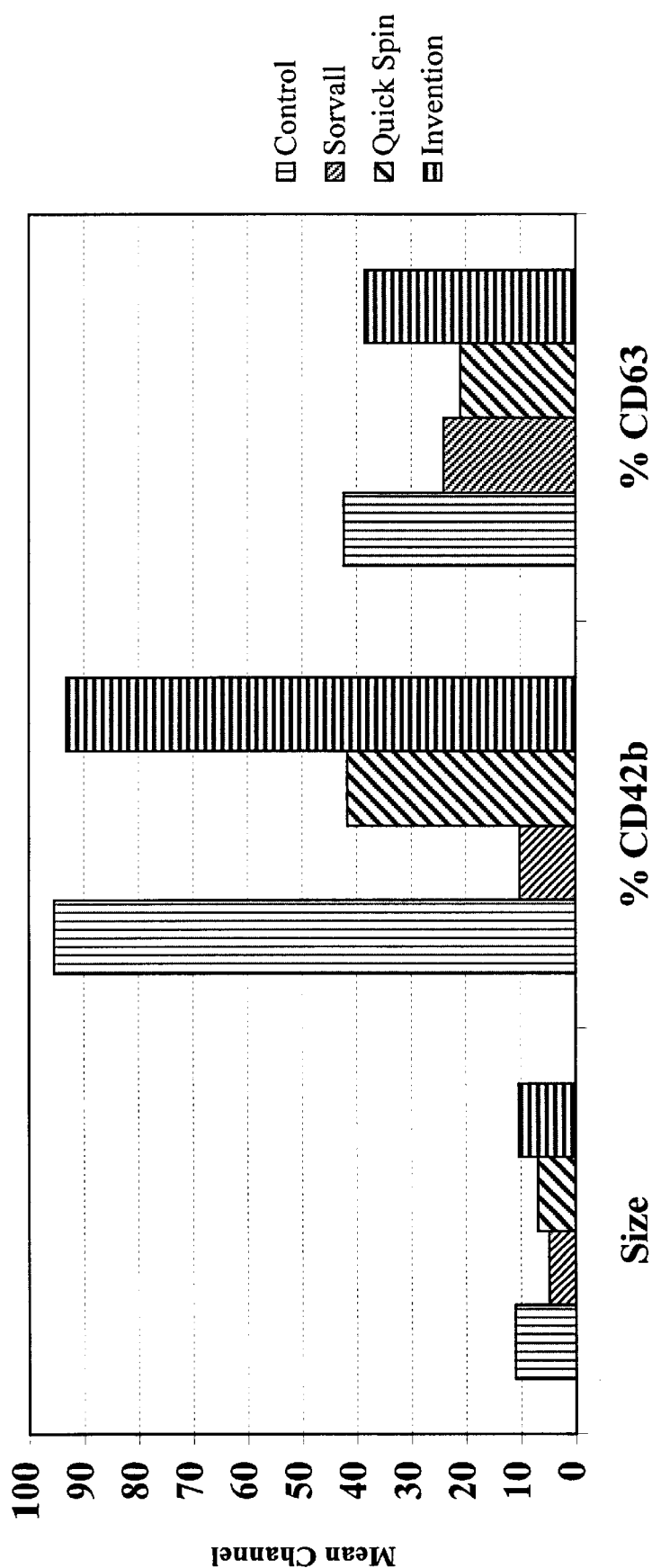
FIG. 11 is a graph showing data obtained from flow cytometric analysis of platelet samples stained for CD42b and CD63. 20 ul of anti-CD42b and 20 ul of anti-CD63 fluorescently-labeled antibodies were incubated with 100 ul of platelet rich plasma (after gravity sedimentation) for 10 minutes without shaking or mixing. "Control" samples were not washed; "Sorvall" samples were washed in a SORVALL® Cellwasher 2 (E.I. du Pont de Nemours) using the AUTO mode per the manufacturers instructions; "Quick Spin" samples were washed according to the Quick Spin protocol described herein; and "Invention" samples were washed one time using a hollow fiber membrane apparatus. Data were obtained using a COULTER® EPICS® XL™ flow cytometer (Beckman Coulter, Inc., Miami, Fla.) and presented as size (determined based on forward and orthogonal light scatter), percent CD42b (mean channel fluorescence), and percent CD63 (mean channel fluorescence). Data shown are averages of three replicates using one donor.
Figure 12:
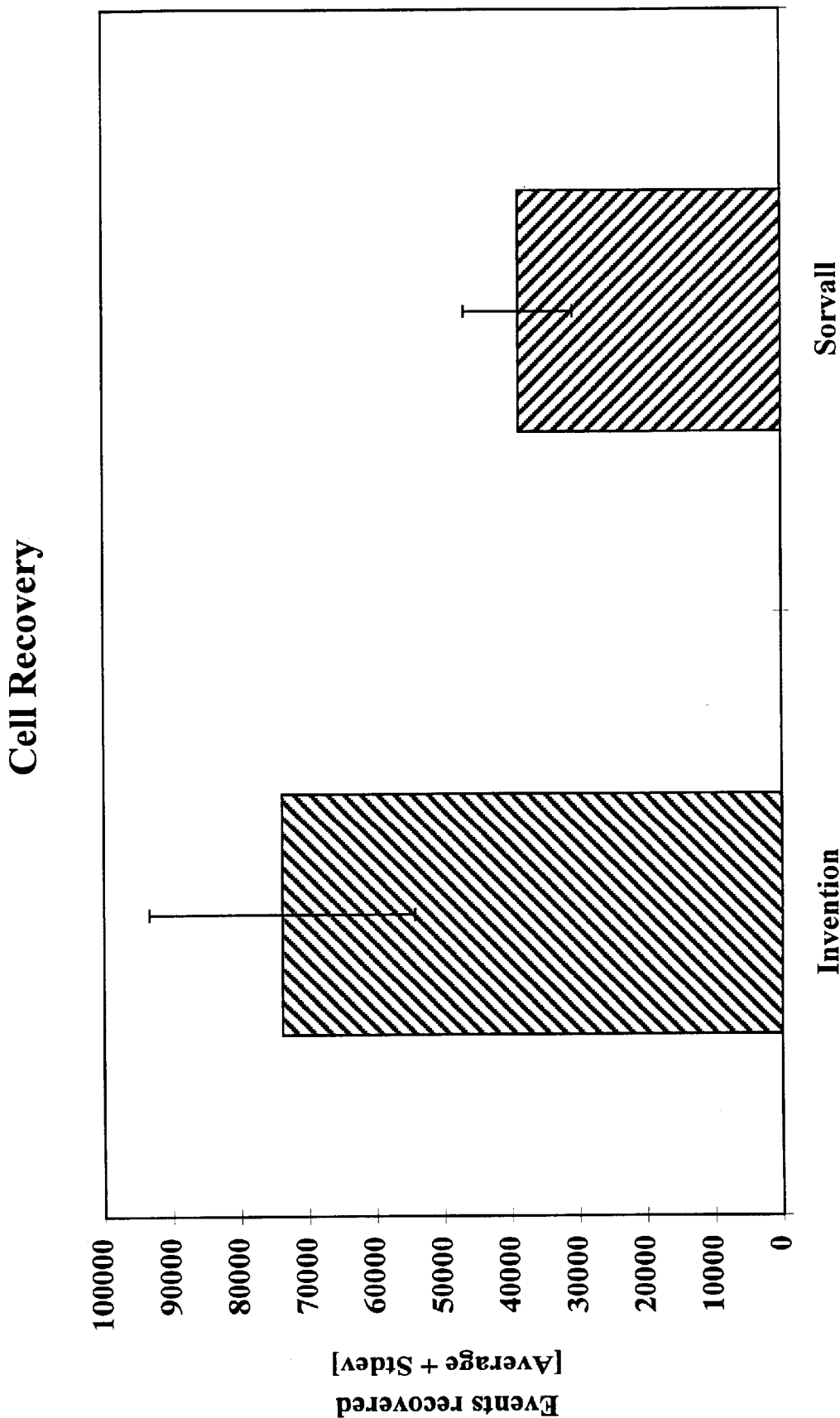
FIG. 12 is a graph showing data obtained from flow cytometric analysis of bone marrow cell samples stained for CD56, erythrocyte-lysed, and fixed using a TQ-Prep™ apparatus (Beckman Coulter, Inc., Miami, Fla.). "Sorvall" samples were washed in a SORVALL® Cellwasher 2 using the AUTO mode per the manufacturers instructions, and "Invention" samples were washed one time using a hollow fiber membrane apparatus. Data were obtained using an EPICS XL flow cytometer and are presented as cell recovery (number of event in a thirty second run) and signal-to-noise ratio (as described herein). Data shown are averages of three donors with one replicate per donor. Error bars represent standard deviation.
Figure 13:
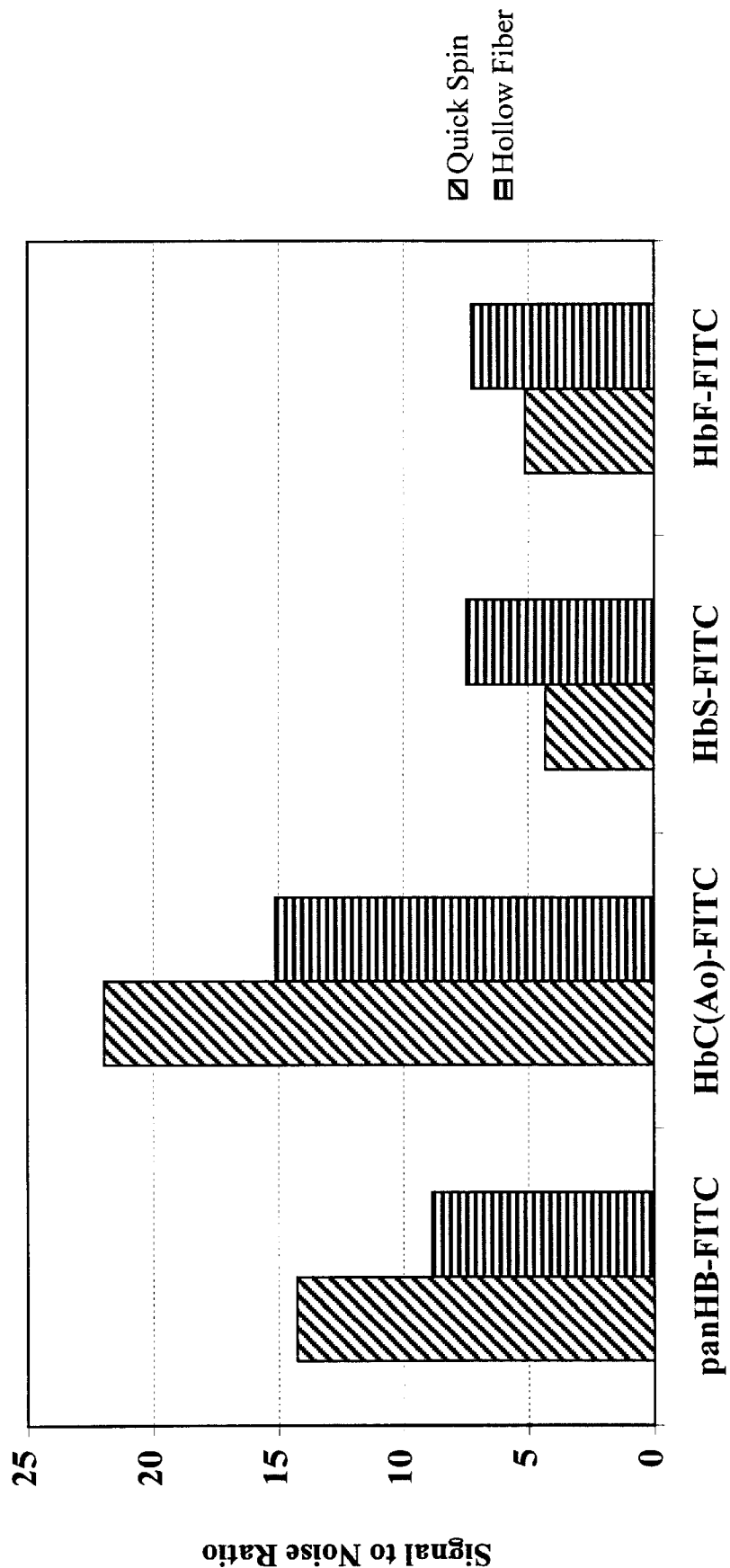
FIG. 13 is a graph showing data obtained from flow cytometric analysis of blood cell samples stained for hemoglobin. 200 ul of whole blood were cross-linked, permeabilized, and stabilized using commercially available reagents according to standard protocols. 20 ul of the prepared permeabilized RBCs were stained with the following amounts of individual antibodies: MsigG1-PE/MsIgG1-FITC-20 ul, PanHb-FITC-10 ul, HbC-FITC-30 ul (cross reactive with HbAo), HbS-FITC-30 ul, HbF-FITC-30 ul, or HbAlc-FITC-10 ul; mixed for 20 min; and then washed. "Quick Spin" samples were washed according to the Quick Spin protocol described herein; and "Invention" samples were washed one time using a hollow fiber membrane apparatus. Data were obtained using an EPICS XL flow cytometer and are presented as signal-to-noise ratios (as described herein). Data shown are based on one replicate per test condition.

For example, referring to FIG. 11, application of the invention to platelet samples is shown by flow cytometric analysis of platelet samples stained for CD42b and CD63. Additionally, as another example, referring to FIG. 12, application of the invention to bone marrow samples is shown by flow cytometric analysis of bone marrow cell samples stained for CD56. Cell recovery and signal-to-noise ratio were comparable between "Invention" which is the apparatus and method described herein and the Sorvall apparatus and washing method. Referring now to FIG. 13, application of the invention for intracellular analysis is shown by flow cytometric analysis of permeabilized blood cell samples stained for hemoglobin. Signal-to-noise ratios were comparable between "Hollow Fiber" which is the apparatus and method described herein and Quick Spin washing method described in Example 2.

EXAMPLE 9

Immunoassay with Analyte Specific Bead

The value of washing a test mixture in cytometer based immunoassay was demonstrated by tests of different protocols for Thyroid Stimulating Hormone (TSH) assay. Separation and washing of analyte specific beads was done by centrifugation: 400 microliters of assay buffer (1% Bovine Serum Albumen, 0.02% Tween 20 in Phosphate Buffer Solution) added to 100 microliters of reaction volume after incubation of capture beads with test sample for two hours. Centrifuged at approximately 20,000 g for 5 minutes. Supernatants discarded and pellet resuspended in 100 microliters of assay buffer. Measured Mean Fluorescence Intensity (MFI) from Coulter Elite cytometer with 650 nm excitation. The dose/response curve for the two step incubation with a wash step between incubations gave a higher MFI at high TSH doses and a lower background MFI without TSH than either a one step incubation or a two step incubation without the wash step. This indicates that washing improves signal to noise ratio for this assay.

A test of the apparatus and method of the present invention demonstrated bead recovery for several bead sizes. Use of a 0.45 micron pore size hollow fiber cartridge with 1 mm bore and 8 $cm^2$ filter area, produced the following bead recoveries following the basic aspirate, filter and recover protocol.

| Bead size | Recovery +/− 5% |
|---|---|
| 10 μm | 83% |
| 15 μm | 102% |
| 20 μm | 103% |

Run to run carry over of beads was 3% or less and became undetectable with an intermediate rinse. This showed that the apparatus and method of the present invention could achieve good bead recoveries with acceptable carryover.

EXAMPLE 10

Washing Apparatus Integrated With an Analyzer

It is specifically envisioned that the cell washing apparatus of the invention can be integrated with one or more conventional analyzers thereby obviating a manual step of transferring a concentration of the composition of interest from the washing device to the analyzer. For example, the washing apparatus described herein could be integrated with a flow cytometer such as a COULTER EPICS® brand flow cytometer by providing robotic means for transferring a test tube from a cell sample washed using the washing apparatus of the invention such that the tube becomes positioned so that it can be analyzed in the flow cytometer. As one example, a conveyor could transport a carousel containing several washed samples from a position suitable for washing the cells (e.g., proximal to the cell washing device) to another position suitable for analyzing the samples (e.g., proximal to the flow cytometer). Fluid connections and conduits would aspirate washed cell samples into the flow cytometer for analysis.

Alternatively, the washing apparatus of the invention can be integrated with one or more analyzing instruments. In this embodiment, the blood cell sample would be washed after lysing the erythrocytes to remove remaining cellular debris. Still further, the blood cell sample could be washed prior to any biological or chemical reaction with the blood cell sample so that interferants are removed from the blood cell sample.

Still further, the present invention has utility in protein purification. The prior art method of purification of protein has focused on the use of packed columns of resins which separate low molecular weight activator from high molecular weight protein. However, the prior art method suffers several disadvantages. In the prior art method, the use of pack columns is expensive because of the cost of the resin, which is not reusable, such as G-50, and the time required to assemble the column and perform the exclusion chromatography. Moreover, in the prior art method, concentration of the eluted purified protein presents additional problems of time and cost. Still further, the present batch method does not clog the hollow fiber filter membrane which would be expected in a flat filtration process and is able to utilize smaller volumes of mixture than would be required in a recirculating pump filtration system.

It has been found that modification of the device shown in FIG. 4A can be used for the purification of an proteinaceous materials, such as antibody or an activated antibody or a fluorescent label or an activated fluorescent label or conjugated antibody fluorescent label and biological macromolecules from 20,000 molecular weight up to 2,000,000 mw, such as nucleic acids or complex carbohydrates. In the antibody, activated antibody, fluorescent label or activated fluorescent label or conjugated antibody fluorescent label embodiments, the apparatus employs a hollow fiber having a pore structure molecular weight cut off range from approximately 1,000 to 50,000. In the biological macromolecules, the apparatus employs a hollow fiber having a pore structure molecular weight cut off range from approximately 3,000 to 5,000. An additional material reservoir for the proteinaceous material or the biological macromolecules is added which is fluidly connected to the filtration device 24 by an additional reservoir hose. Alternatively, the detergent solution reservoir 58 can be replaced with the additional reservoir. In a similar configuration, the protein or the biological macromolecules to be purified can be added to the filtration device by any convenient means such that the protein or the biological macromolecules enters the lumen 66.

The present method for purification of a proteinaceous material from a mixture of the proteinaceous material and interferants comprises supplying a first end of a hollow fiber filter with a mixture of a proteinaceous material having a molecular weight between approximately 20,000 and 2,000,000 and interferants having a molecular weight that is less than 50%, preferably less than 90%, and most preferably less than 1% of the molecular weight of the proteinaceous material to a first end of a hollow fiber filter; applying a vacuum pressure force to chamber containing the hollow fiber filter or a positive pressure force into the lumen of the hollow fiber filter to cause the interferants in the mixture to pass through the membrane of the hollow fiber filter, adding buffer or other fluid which does not react with the proteinaceous material to further cause the interferant to pass through the membrane of the hollow fiber filter and recovering the proteinaceous material from a second end of the hollow fiber filter, said second end being disposed at an opposite end of the hollow fiber filter from the first end.

In this embodiment, the recovery of the proteinaceous material from the mixture is greater than 90%, preferably greater than 95% and most preferably greater than 99% from the mixture. Moreover, in this embodiment, the concentration of the proteinaceous material in the retenate from the hollow fiber filter would be greater than approximately 40%, preferably greater than 50% and most preferably greater than 60%. More specifically, in the method of the present invention, the original volume of the mixture containing the proteinaceous material is reduced in volume such that the concentration of the proteinaceous material in the retenate is greater than 40%, preferably greater than 50% and most preferably greater than 60%. The concentration feature is a function of the hollow fiber filter void volume and the amount of buffer that is used to recover the proteinaceous mater. Therefore, the prior art problems of concentrating the eluted purified protein proteinaceous material from the column is eliminated.

The present method for purification of a biological macromolecule from a mixture of the biological macromolecule and interferants comprises supplying a first end of a hollow fiber filter with a mixture of a biological macromolecule having a molecular weight between approximately 20,000 and 2,000,000 and interferants having a molecular weight that is less than 50%, preferably less than 90%, and most preferably less than 1% of the molecular weight of the biological macromolecule to a first end of a hollow fiber filter; applying a vacuum pressure force to chamber containing the hollow fiber filter or a positive pressure force into the lumen of the hollow fiber filter to cause the interferants in the mixture to pass through the membrane of the hollow fiber filter, adding buffer or other fluid which does not react with the biological macromolecule to further cause the interferant to pass through the membrane of the hollow fiber filter and recovering the biological macromolecule from a second end of the hollow fiber filter, said second end being disposed at an opposite end of the hollow fiber filter from the first end. The interferants are typically glutaraldehyde, 1-ethyl-3-(3'-dimethylaminopropyl-carbodiimide)-hydrochloride (EDAC) and other lower molecular hetero- and homo-bifunctional linkers having a molecular weight in range under 1,000.

In this embodiment, the recovery of the biological macromolecule from the mixture is greater than 20%, preferably greater than 30% and most preferably greater than 35% from the mixture. Moreover, in this embodiment, the concentration of the biological macromolecule in the retenate from the hollow fiber filter would be greater than approximately 20%, preferably greater than 30% and most preferably greater than 35%. More specifically, in the method of the present invention, the original volume of the mixture containing the biological macromolecule is reduced in volume such that the concentration of the biological macromolecule in the retenate is greater than 20%, preferably greater than 30% and most preferably greater than 35%. The recovery rate is comparable to prior art methods of ethanol precipitation due the fragile nature of the RNA. The concentration feature is a function of the hollow fiber filter void volume and the amount of buffer that is used to recover the biological macromolecule. Therefore, the prior art problems of concentrating the eluted purified biological macromolecule from the column is eliminated. As can be seen from Example 13, there is some improvement in recovery compared with ethanol precipitation, but one of the significant advantages of the present method is the time necessary to purify the nucleic acid. Considering similar batch sizes of 300 to 500 ml, precipitation takes approximately three days while using the method of the present invention takes 3 to 4 hours.

EXAMPLE 11

Purification of Proteinaceous Material

Purification of CD4 Monoclonal Antibody From Fluorescein

This experiment was conducted to prove the feasibility of replacement of size exclusion gel filtration chromatography for purification, separation and concentration of a biologically active proteinaceous materials from the low molecular weight activating reagents.
Materials: The following materials were used:
A/G hollow fiber filter cartridge, P/N UFP-10-C-3A, 10,000 MWC
Peristaltic pump assembly, with tubings, valves and fittings.
Spectrophotometer, cuvettes and fraction collection tubes.
CD4 antibody, 39.15 mg/ml
PBS powdered
Fluorescein, molecular weight approximately 400–500, SIGMA Chemical
Deionized water.
Spectrophotometer.
Method: A hollow fiber filter cartridge (void volume 3 ml) was flushed with 150 ml of 1× PBS solution, to remove any presence of glycerol, used by manufacturer for long term storage and left filled with 1× PBS. Bottom entrance to the cartridge had 3-way valve installed. Top entrance to the cartridge had 3-way valve installed and connected to peristaltic (vacuum) pump. Lower waste port of the cartridge had 3-way valve installed and connected to peristaltic (vacuum) pump. Upper waste port of the cartridge was blocked. Solution of CD4 antibody in 1× PBS was prepared at 1 mg/ml. Solution of fluorescein in 1× PBS was prepared at 0.015 mg/ml. A part of CD4 solution was diluted twice with 1× PBS to obtain 0.5 mg/ml control. A part of fluorescein solution was diluted twice with 1× PBS to obtain 0.0075 mg/ml control. Both controls were scanned on spectrophotometer between 250 and 600 nm. The equal volumes of 3 ml of CD4 at 1.0 mg/ml and 3 ml of fluorescein at 0.015 mg/ml were mixed together and scanned in the same wave length range, as the unseparated control. CD4 gave absorbance peak at 276 nm, while fluorescein at 490 nm. Lower waste port valve was turned to allow evacuation of the hollow fiber filter cartridge. Top entrance valve was closed toward the cartridge. Bottom entrance valve was open to allow sample aspiration by vacuum force. Peristaltic pump was started and 6 ml of sample mixture was aspirated into the lumens of the hollow fiber filter cartridge. The valve at the top entrance to the hollow fiber filter cartridge was turned so as to allow the dialyzing buffer (1× PBS) to flow into the cartridge's lumens, containing antibody/fluorescein mixture. A container with the same dialyzing buffer was placed under the aspiration tip of the hollow fiber filter cartridge. Peristaltic pump was started again and the vacuum force has started to draw the dialyzing buffer (1× PBS) through the top and bottom entrances to the hollow fiber filter cartridge, thus providing diafiltration of CD4/fluorescein and well mixing it at the same time. Samples of permeate (filtrate), containing fluorescein were collected and scanned at 250–600 nm wave length range. Permeate collection was stopped, when there was no detectable fluorescein in the permeate. At this point, lower waste port valve was turned as to stop any flow in or out of that port. Bottom entrance valve was turned to provide the 1× PBS flow from the top to the bottom of the HF cartridge as to allow to collect CD4 antibody with fluorescein completely removed. Peristaltic pump was turned on in reverse to provide 1× PBS flow through the top entrance of the cartridge and to flush out all the CD4 antibody. Two samples of recovered CD4 antibody were scanned on spectrophotometer to obtain the values for recovered CD4 antibody and to verify the absence of fluorescein peak. Combined values of CD4 absorbance in two collected fractions resulted in 92.5% of CD4 recovery.
Conclusion: The size of hollow fiber filter cartridge used, was larger than necessary for the CD4/fluorescein sample size of only 3mg, based on CD4. Either a larger CD4 sample or smaller hollow fiber filter cartridge will produce much closer to 100% recovery.

EXAMPLE 12

Separation of Activated Monoclonal Antibody from Low Molecular Weight Activator

The materials of Example 11 are used, except the CD 4 antibody has been activated by processes known to those skilled in the art which activates the amino groups of the antibody, and the fluorescein is eliminated in place of the activator which has a molecular weight of approximately 400–500 MW. The method of Example 11 is repeated with a larger volume of the mixture of the activated monoclonal antibody and activator, i.e. 50 milliliters. The resulting recovery of the antibody in the retentate would be approximately 99% activated antibody and the concentration of the antibody in the retenate would be greater than approximately 50%.

EXAMPLE 13

Separation of Free Glutaraldehyde from a Mixture of RNA and Free Glutaraldehyde

The materials of Example 11 are used, except the hollow fiber filter cartridge, has a 5,000 molecular weight cutoff, the CD 4 antibody has been replace with a reacted RNA with glutaraldehyde by processes known to those skilled in the art which activates the amino groups of the nucleic acid, and the fluorescein is eliminated in place of the unreacted free glutaraldehyde which has a molecular weight of approximately 100 MW. The method of Example 11 is repeated with a larger volume of the mixture of the reacted RNA and free glutaraldehyde, i.e. 500 milliliters. The following information is a specific procedure for the separation of free glutaraldehyde from a mixture of RNA and free glutaraldehyde.

1.1 500 ml of RNA (50 mg/ml) is mixed with specified volume of 25% glutaraldehyde.
1.2 Mixture incubated to allow reaction of glutaraldehyde with amino groups of RNA bases
1.3 Remove excess (free) glutaraldehyde (MW=100.12) from reacted RNA-glutaraldehyde (MW range from= 30,000 to >100,000) using hollow fiber filter with 5,000 MWCO.
   1.3.1 Wash with 1 L 0.1 M KOH to decontaminate filter lumen
   1.3.2 Wash with 5 L sterilized $H_2O$ to wash away KOH
   1.3.3 Wash with 2 L application-appropriate buffer 1.3.4 Load RNA-glut reaction mixture.
1.3.5 Wash with 2 L application-appropriate buffer (free glutaraldehyde removed in this step.
1.3.6 Collect 250 ml reacted RNA-glutaraldehyde.
1.3.7 Clean hollow fiber filter by repeating steps 1.3.1 and 1.3.2.

Determine RNA concentration using spectrophotometer. Recovery ranges from 20 to 43%, average=32.7%, compared to recovery of 12 to 45%, average of 25.4% for precipitation of RNA using ethanol.

While the above specification contains many specifics, these should not be construed as limitations on the scope of the invention, but rather as examples of preferred embodiments thereof. Many other variations are possible. For example, the invention includes an apparatus for removing interferants from a cell sample that has only one hydraulic force transducer rather than two pumps and a vacuum source. The various hoses and valves within this apparatus can be connected in a manner to cooperate with the sole hydraulic force transducer, so that the apparatus functions much as the described preferred embodiments. As another example, a method of concentrating a cell sample by removing liquid from the sample using a microporous hollow fiber membrane is included within the invention. Accordingly, the scope of the invention should be determined not by the embodiments illustrated, but by the appended claims and their legal equivalents.

What is claimed is:

1. An automated method for removing interferants from a mixture containing a composition of interest and interferants comprising:

a) applying a vacuum force to a first container containing said mixture to cause said mixture to contact a filtration device comprising:
      i. an impermeable housing that forms an extramembrane chamber wherein said housing contains at least three ports and wherein at least one tort is connected by a conduit to the vacuum source; and
      ii. a filter in said chamber that selectively retains said composition of interest while allowing interferants to pass through the filter, said filter comprising a microporous hollow fiber membrane having a plurality of pores, wherein the microporous hollow fiber membrane is fashioned into at least one tube defining a lumen, said tube having a first opening at one end of the tube, and a second opening at the opposite end of the tube, wherein said mixture enters said filter at said first opening;

b) applying a force transversely through said filter to said mixture in contact with the filter to separate the composition of interest from the mixture of the composition of interest and interferants, said force causing said interferants to pass transversely through said filter with the composition of interest retained in the lumen of the filter; and c) recovering the composition of interest from the filter by passing a buffer through the lumen of the filter, said buffer applied at said second opening at the opposite end of said tube.

2. The method of claim 1, wherein said composition of interest comprises an analyte specific bead.

3. The method of claim 2, wherein said recovering step comprises recovering the analyte specific bead from the filter by providing a sufficient amount of a buffer to contact said filter and analyte specific bead to cause said bead to be removed from said filter into a container.

4. The method of claim 3, wherein the bead removed from the filter is recovered into a second container which is different than the first container.

5. The method of claim 3, wherein the method is performed in less than 5 minutes.

6. The method of claim 3, which further comprises analyzing the bead which is recovered from the filter by electrical or optical measurements.

7. The method of claim 1, wherein the force which enables the interferants in the mixture to pass through the filter is a vacuum force.

8. The method of claim 1, which further comprises diluting the mixture wit a buffer prior to applying the force which enables the interferants in the mixture to pass through the filter.

9. The method of claim 8, wherein diluting the mixture with a buffer comprises diluting the mixture with at least one volume of buffer to each volume of mixture.

10. The method of claim 1, which further comprises analyzing the composition of interest which is recovered from the filter by electrical or optical measurements.

* * * * *